US011506662B2

(12) United States Patent
Heller et al.

(10) Patent No.: US 11,506,662 B2
(45) Date of Patent: Nov. 22, 2022

(54) DETECTION, IDENTIFICATION, AND PURIFICATION OF DEGRADATIVE AND NON-DEGRADATIVE ENZYMES IN BIOLOGICAL SAMPLES

(71) Applicant: The Regents of the University of California, Oakland, CA (US)

(72) Inventors: Michael J. Heller, Poway, CA (US); Augusta E. Modestino, Portland, OR (US); Geert W. Schmid Schonbein, Del Mar, CA (US); Elaine Skowronski, Encinitas, CA (US); Christian Leiterer, Thuringen (DE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/341,385

(22) PCT Filed: Oct. 11, 2017

(86) PCT No.: PCT/US2017/056163
§ 371 (c)(1),
(2) Date: Apr. 11, 2019

(87) PCT Pub. No.: WO2018/071556
PCT Pub. Date: Apr. 19, 2018

(65) Prior Publication Data
US 2020/0057065 A1    Feb. 20, 2020

Related U.S. Application Data

(60) Provisional application No. 62/406,781, filed on Oct. 11, 2016.

(51) Int. Cl.
*G01N 33/573*     (2006.01)
*C07K 14/81*      (2006.01)
*C12N 9/64*       (2006.01)

(52) U.S. Cl.
CPC .......... *G01N 33/573* (2013.01); *C07K 14/81* (2013.01); *C12N 9/6421* (2013.01); *G01N 2333/95* (2013.01)

(58) Field of Classification Search
CPC . C07K 7/06; C07K 7/08; C07K 14/81; C12N 9/6421; C12Q 1/37; G01N 33/573; G01N 2333/95
See application file for complete search history.

(56) References Cited

U.S. PATENT DOCUMENTS

| 2002/0142351 | A1 | 10/2002 | Diamond |
| 2007/0141624 | A1 | 6/2007 | Winn |
| 2010/0280414 | A1 | 11/2010 | Haywood et al. |
| 2010/0285573 | A1 | 11/2010 | Leek et al. |
| 2011/0065127 | A1 | 3/2011 | Heller et al. |
| 2014/0079632 | A1 | 3/2014 | Augustyns et al. |
| 2015/0094449 | A1* | 4/2015 | Heller .................... G01N 33/53 530/327 |
| 2016/0039732 | A1 | 2/2016 | Gayet et al. |
| 2016/0039792 | A1 | 2/2016 | Bogyo et al. |
| 2016/0169885 | A1 | 6/2016 | Heller et al. |

FOREIGN PATENT DOCUMENTS

| CN | 1281346 | 1/2001 | |
| CN | 1697880 | 11/2005 | |
| WO | WO-2014145257 A2 * | 9/2014 | ........... C07D 401/14 |
| WO | WO 2018/071556 | 4/2018 | |

OTHER PUBLICATIONS

Lefkowitz et al. ("An electrophoretic method for the detection of chymotrypsin and trypsin activity directly in whole blood." Electrophoresis 31.2 (2010): 403-410.) (Year: 2010).*
Sigma P2714 Datasheet (published Dec. 20, 2009) . (Year: 2009).*
Extended European Search Report in European Appln. No. 17860762, dated Oct. 17, 2019, 7 pages.
Aebersold et al., "Mass spectrometry-based proteomics," Nature, 2003, 422(6928):198-207.
Baragi et al., "A versatile assay for gelatinases using succinylated gelatin," Afatrix Biol., 2000 19(3):267-273.
Barrett, "Bioinformatics of proteases in the MEROPS database," Curr. Opin. Drug. Discov. Dev., 2004, 7(3):334-341.
Blum et al., "Noninvasive optical imaging of cysteine protease activity using fluorescently quenched activity-based probes," Nat. Chem. Biol., 2003, 3:668-677.
Bremer et al., "In vivo molecular target assessment of matrix metalloproteinase inhibition," Nature Medicine, 2001, 7(6):743-748.
Chan et al., "Developing photoactive affinity probes for proteomic profiling: hydroxamate-based probes for metalloproteases," J Am. Chem. Soc., 2004, 126:14435-14446.
Chen et al., "Developing a strategy for activity-based detection of enzymes in a protein microarray," ChemBioChem, 2003, 4(4):336-339.
Chun et al., "Stereoselective synthesis of photoreactive peptidomimetic γ-secretase inhibitors," J Org. Chem., 2004, 69(21):7344-7347.
Cohen, "The origins of protein phosphorylation," Nat. Cell Biol., 2002, 4:E127-E130.
Coussens et al., "Matrix metalloproteinase inhibitors and cancer: trials and tribulations," Science, 2002, 295:2387-2392.
Crawford et al., "Ontogeny and regulation of matrix metalloproteinase activity in the zebrafish embryo by in vitro and in vivo zymography," Dev. Biol., 2005, 286(2):405-414.
Daviet et al., "Targeting ubiquitin specific proteases for drug discovery," Biochimie (Paris), 2008, 90(2):270-283.

(Continued)

*Primary Examiner* — Sahana S Kaup

(74) *Attorney, Agent, or Firm* — Fish & Richardson P.C.

(57) ABSTRACT

Provided are methods of identifying, visualizing and purifying proteases from a complex biological sample.

12 Claims, 22 Drawing Sheets

Specification includes a Sequence Listing.

(56) References Cited

OTHER PUBLICATIONS

Dean et al., "Proteomics discovery of metalloproteinase substrates in the cellular context by iTRAQ labeling reveals a diverse MMP-2 substrate degradome," Mol. Cell Proteomics, 2007, 6:611-623.
Dornon et al., "Mass spectrometry and protein analysis," Science, 2006, 312:212-217.
Drag et al., "Emerging principles in protease-based drug discovery," Nat. Rev. Drug Discovery, 2010, 9(9):690-701.
Edington et al., "Functional Imaging of Proteases: Recent Advances in the Design and Application of Substrate-Based and Activity-Based Probes," Curr. Opin. Chem. Bio., 2011, 15:785-805.
Eppinger et al., "Enzyme Microarrays: On-Chip Determination of Inhibition Constants Based on Affinity Label Detection of Enzymatic Activity," Angew. Chem., 2004, 116:3894-3898.
Funeriu et al., "Enzyme family-specific and activity-based screening of chemical libraries using enzyme microarrays," Nat. Biotechnol., 2005, 23(5):622-627.
Geiss-Friedlander et al., "Concepts in sumoylation: a decadeon," Nat. Rev. Mol. Cell Biol., 2007, 8:947-956.
Grabarek et al., "In situ activation of caspases and serine proteases during apoptosis detected by affinity labeling their enzyme active centers with fluorochrome-tagged inhibitors," Exp. Hematol., 2002, 30(9):982-989.
Greenbaum et al., "Chemical approaches for functionally probing the proteome," Mol. Cell. Proteomics, 2002, 1:60-68.
Greenbaum et al., "Epoxide electrophiles as activity-dependent cysteine protease profiling and discoveiy tools," Chem. Biol., 2000 7(8):569-581.
Gutierrez-Fernandez, "Matrix metalloproteinase-8 functions as a metastasis suppressor through modulation of tumor cell adhesion and invasion," Cancer Res., 2008, 68(8):2755-2763.
Hegedus et al., "Additional MDA-MB-231 breast cancer cell matrix metalloproteinases promote invasiveness," J Cell. Physiol., 2008, 216(2):480-485.
International Preliminary Report on Patentability in International Appln. No. PCT/US2017/056163, dated Apr. 16, 2019, 11 pages.
International Search Report and Written Opinion in International Appln. No. PCT/US2017/056163, dated Dec. 26, 2017.
Kaberdin et al., "Expanding the use of zymography by the chemical linkage of small, defined substrates to the gel matrix," Genome Res., 2003, 13:1961-1965.
Kaijzel et al., "Whole-body optical imaging in animal models to assess cancer development and progression," Clin. Cancer Res., 2007, 13(12):3490-3497.
Keow et al., "Activity-based labeling of matrix metalloproteinases in living vertebrate embryos," PLoS ONE, 2012, 7:e43434.
Kessler et al., "Extended peptide-based inhibitors efficiently target the proteasome and reveal overlapping specificities of the catalytic beta-subunits," Chem. Biol., 2001, 8(9):913-929.
Kidd et al., "Profiling serine hydrolase activities in complex proteomes," Biochemistry, 2001, 40:4005-4015.
Kleiner et al., "Quantitative zymography: detection of picogram quantities of gelatinases," Anal. Biochem., 1994, 218(2):325-329.
Kupai, K. et al., "Matrix metalloproteinase activity assays: importance of zymography," J. Pharmacol. Toxicol. Methods, 2010, 61(2):205-209.
Liu et al., "Activity-based protein profiling: the serine hydrolases," Proc. Natl. Acad Sci. USA, 1999, 96(26):14694-14699.
Lopez-Otin et al., "Protease degradomics: a new challenge for proteomics," Nat. Rev. Mol. Cell Biol., 2002, 3:509-519.
Mann et al., "Analysis of proteins and proteomes by mass spectrometry," Annu. Rev. Biochem., 2001, 70:437-473.
McKerrow et al., "Purification and characterization of an elastinolytic proteinase secreted by cercariae of Schistosoma mansoni," J Biol. Chem., 1985, 260(6):3703-3707.
McQuibban et al., "Inflammation dampened by gelatinase A cleavage of monocyte chemoattractant protein-3," Science, 2000, 289(5482):1202-1206.
McQuibban et al., "Matrix metalloproteinase processing of monocyte chemoattractant proteins generates CC chemokine receptor antagonists with anti-inflammatory properties in vivo," Blood, 2002, 100(4):1160-1167.
Modestino et al., "Thrombin Generation Assay in Untreated Whole Human Blood," Electrophoresis, 2016, 37:2248-2256.
Moldoveanu et al., "A Ca(2+) switch aligns the active site of calpain," Cell, 2002, 108(5):649-660.
Nandi et al., "The ubiquitin-proteasome system," J. Biosci., 2006, 31(1):137-155.
O'Donoghue et al., "Global identification of peptidase specificity by multiplex substrate profiling," Nature Methods, 9(11):1095-1100.
Overall et al., "Towards third generation matrix metalloproteinase inhibitors for cancer therapy," Br. J. Cancer, 2006, 94:941-946.
Overall et al., "Tumour microenvironment—opinion: validating matrix metalloproteinases as drug targets and anti-targets for cancer therapy," Nat. Rev. Cancer, 2006, 6:227-239.
Overall, C. M., "Protease degradomics: mass spectrometry discovery of protease substrates and the CLIP-CHIP, a dedicated DNA microarray of all human proteases and inhibitors," Biol. Chem., 2004, 385(6):493-504.
Paemen et al., "The gelatinase inhibitory activity of tetracyclines and chemically modified tetracycline analogues as measured by a novel microtiter assay for inhibitors," Biochem. Pharmacol. 1996, 52(1):105-111.
Pease et al., "Light-generated oligonucleotide arrays for rapid DNA sequence analysis," Proc. Natl. Acad Sci. USA, 1994, 91:5022-5026.
Piccard et al., "'Reverse degradomics', monitoring of proteolytic trimming by multi-CE and confocal detection of fluorescent substrates and reaction products," Electrophoresis, 2009, 30(13):2366-2377.
Polevoda et al., "N-terminal acetyltransferases and sequence requirements for N-terminal acetylation of eukaiyotic proteins," J. Mol. Biol., 2003, 325(4):595-622.
Puente et al., "Human and mouse proteases: a comparative genomic approach," Nat. Rev. Genet., 2003 4:544-558.
Sadoul et al., "Regulation of protein turnover by acetyltransferases and deacetylases," Biochimie (Paris), 2008, 90(2):306-312.
Saghatelian et al., "Activity-based probes for the proteomic profiling of metalloproteases," Proc. Natl. Acad. Sci. USA, 2004, 101(27):10000-10005.
Scherer et al., "Optical imaging of matrix metalloproteinase-7 activity in vivo using a proteolytic nanobeacon," Mol. Imaging, 2008, 7(3)118-131.
Schmidinger et al., "Activity-based proteomics: enzymatic activity profiling in complex proteomes," Amino Acids, 2006, 30(4):333-350.
Schwartz et al., "Hu/Mu Protin oligonucleotide microarray: dual-species array for profiling protease and protease inhibitor gene expression in tumors and their microenvironment," Mol. Cancer Res., 2007, 5, 443-54.
Sieber et al., "Microarray platform for profiling enzyme activities in complex proteomes," J. Am. Chem. Soc., 2004, 126:15640-15641.
Stoch et al., "Cathepsin K inhibitors: a novel target for osteoporosis therapy," Clin. Pharmacol. Ther., 2008, 83(1):172-176.
Thornberry, N. A., "Inactivation of interleukin-1β converting enzyme by peptide (acyloxy)methyl ketones," Biochemistry, 1994, 33:3934-3940.
Tremblay et al., "Anti-inflammatory activity of neutrophil elastase inhibitors," Curr. Opin. Investig. Drugs, 2003, 4(5):556-565.
Turk et al., "Lysosomal cysteine proteases: facts and opportunities," EMBO J, 2001, 20:4629-4633.
Turk, "Targeting proteases: successes, failures and future prospects," Nat. Rev. Drug Discov., 2006, 5:785-799.
Uttamchandani et al., "Activity-based fingerprinting and inhibitor discovery of cysteine proteases in a microarray," Chem. Commun., 2007, 1518-1520.
Vandooren et al., "Gelatin degradation assay reveals MMP-9 inhibitors and function of O-glycosylated domain," World J. Biol. Chem., 2011, 2(1):14-24.
Walsh et al., "Post-translational modifications in the context of therapeutic proteins," Nat. Biotechnol., 2006, 24:1241-1252.

(56) References Cited

OTHER PUBLICATIONS

Wang et al., "Biochemical analysis of the 20 S proteasome of *Trypanosoma brucei*," J. Biol. Chem., 2003, 278(18):15800-15808.

Weissleder et al., "In vivo imaging of tumors with protease-activated near-infrared fluorescent probes," Nat. Biotechnol., 1999, 17(4):375-378.

Wilkesman et al., "Protease analysis by zymography: a review on techniques and patents," Recent Pat. Biotechnol., 2009, 3:175-184.

Williams et al., "Zymogen/enzyme discrimination using peptide chloromethyl ketones," J Biol. Chem., 1989, 264(13):7536-7545.

Winssinger et al., "PNA-encoded protease substrate microarrays," Chem. Biol., 2004, 11(10):1351-1360.

Wu et al., "A peptide aldehyde microarray for high-throughput profding of cellular events," J Am. Chem. Soc., 2011, 133(6):1946-1954.

Wyatt et al., "The zebrafish embryo: a powerful model system for investigating matrix remodeling," Zebrafish, 2009, 6(4):347-354.

Yang et al., "Increased expression of human macrophage metalloelastase (MMP-12) is associated with the invasion of endometrial adenocarcinoma," Pathol. Res. Pract., 2007, 203(7):499-505.

Yang et al., "Modification of Hydrophilic and Hydrophobic Surfaces Using an Ionic-Complementary Peptide," PLoS One, 2007, 2:1-11.

\* cited by examiner

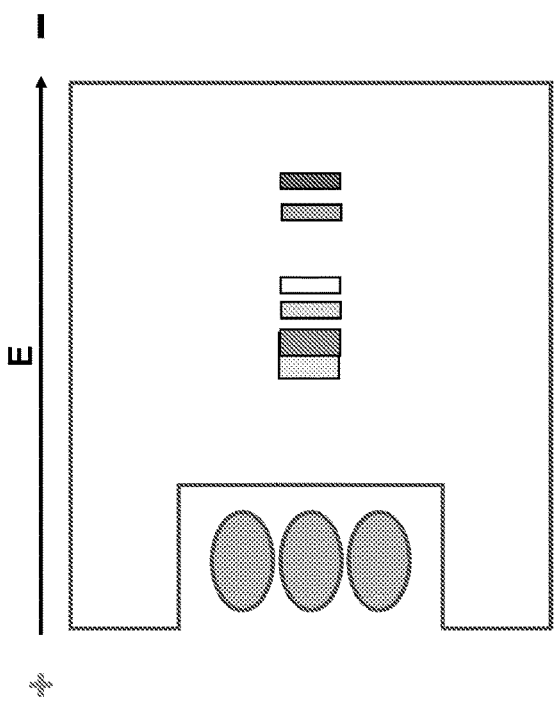
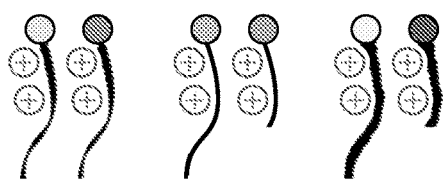
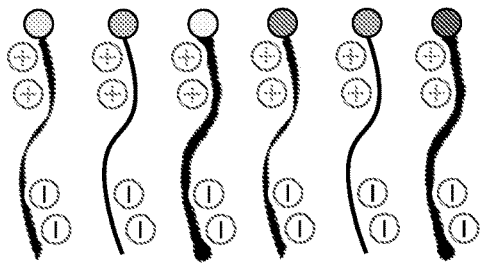
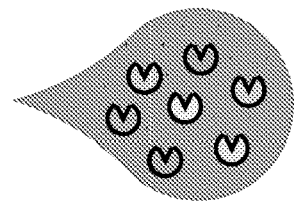
Fig. 1A

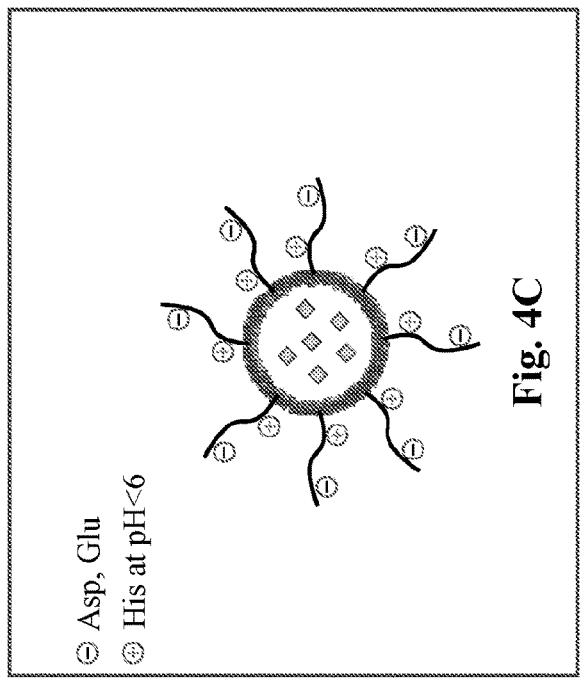
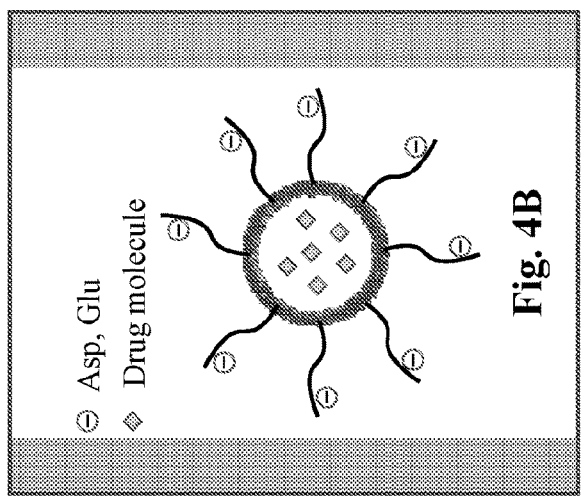
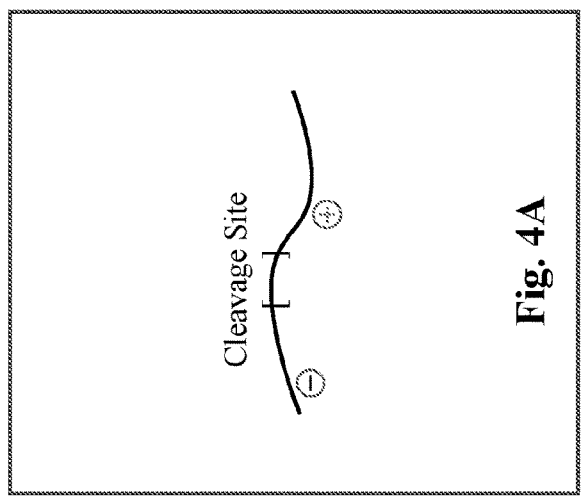
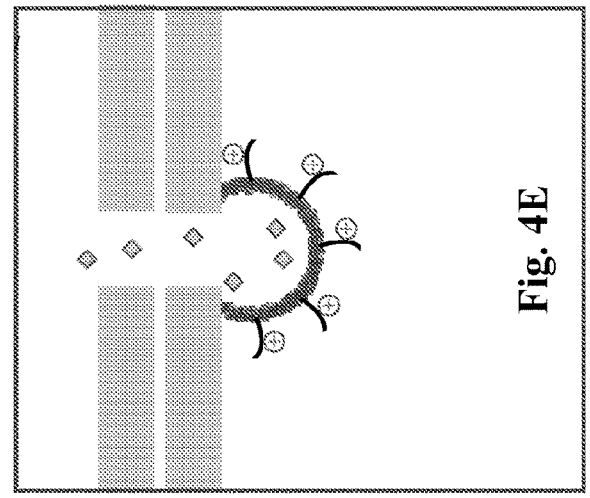
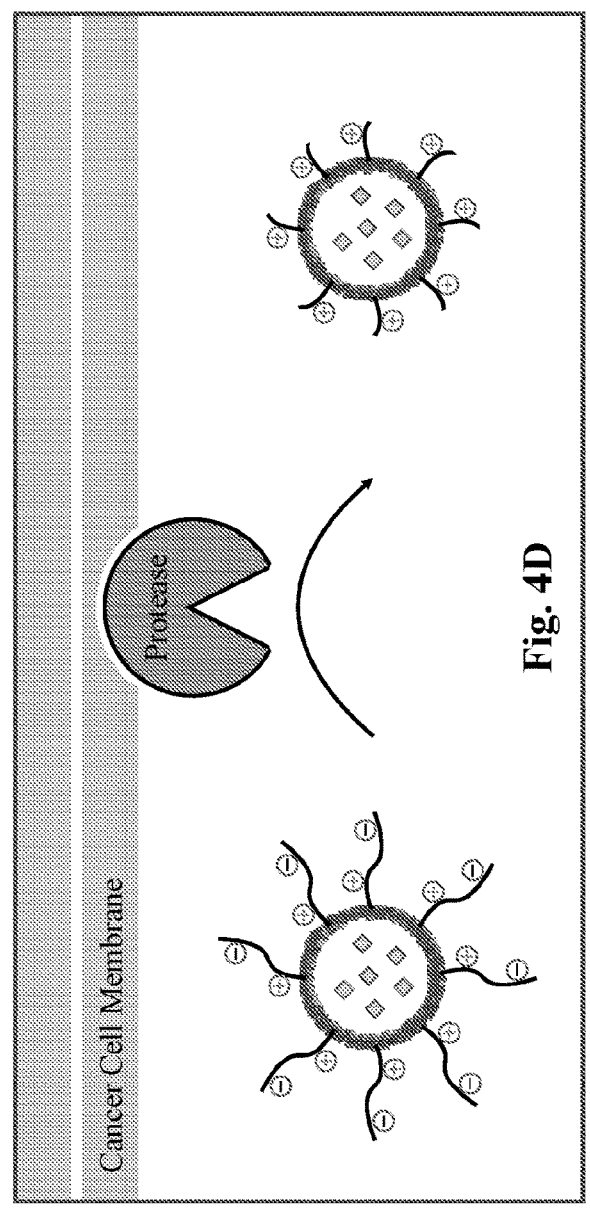

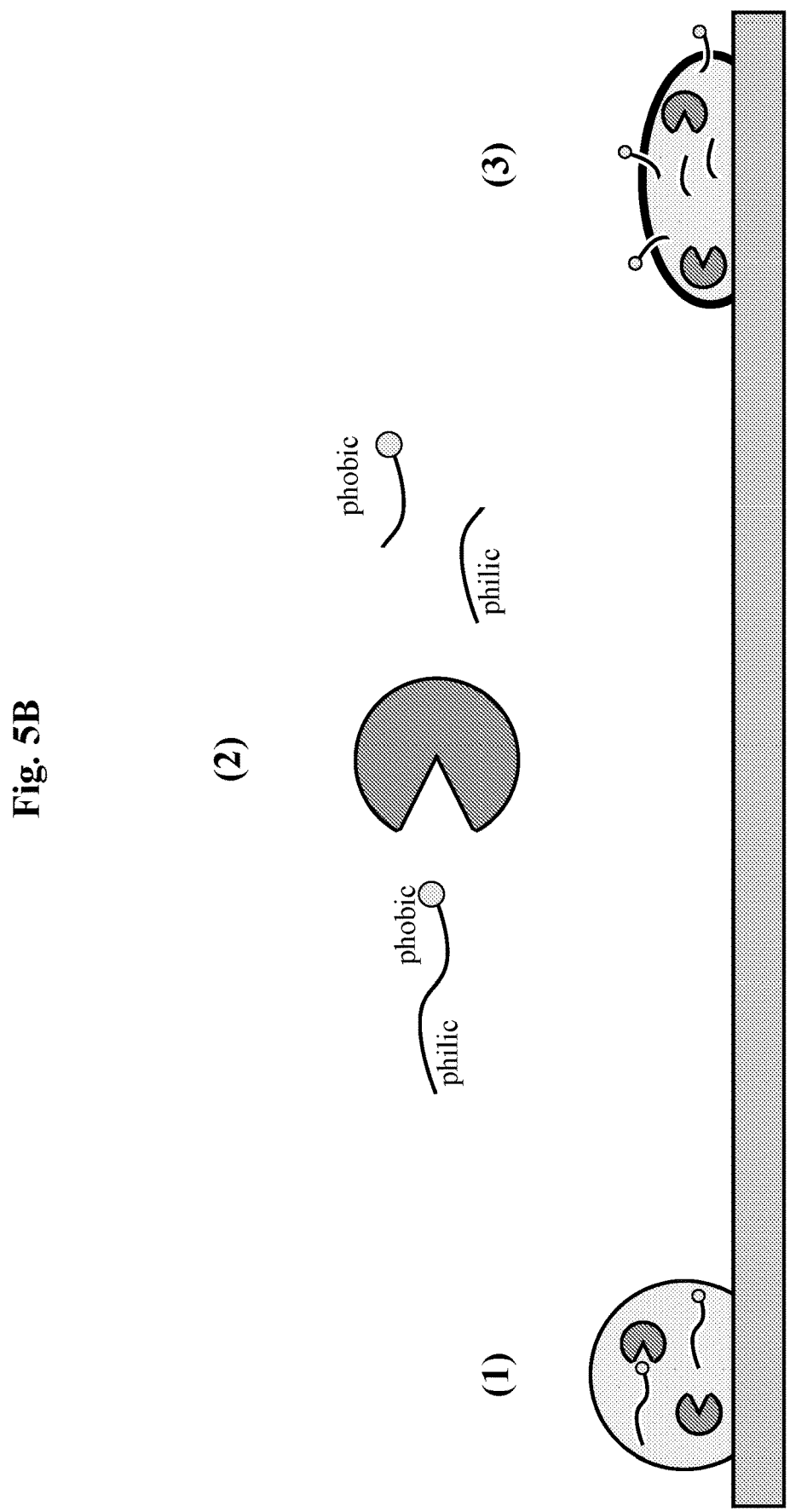

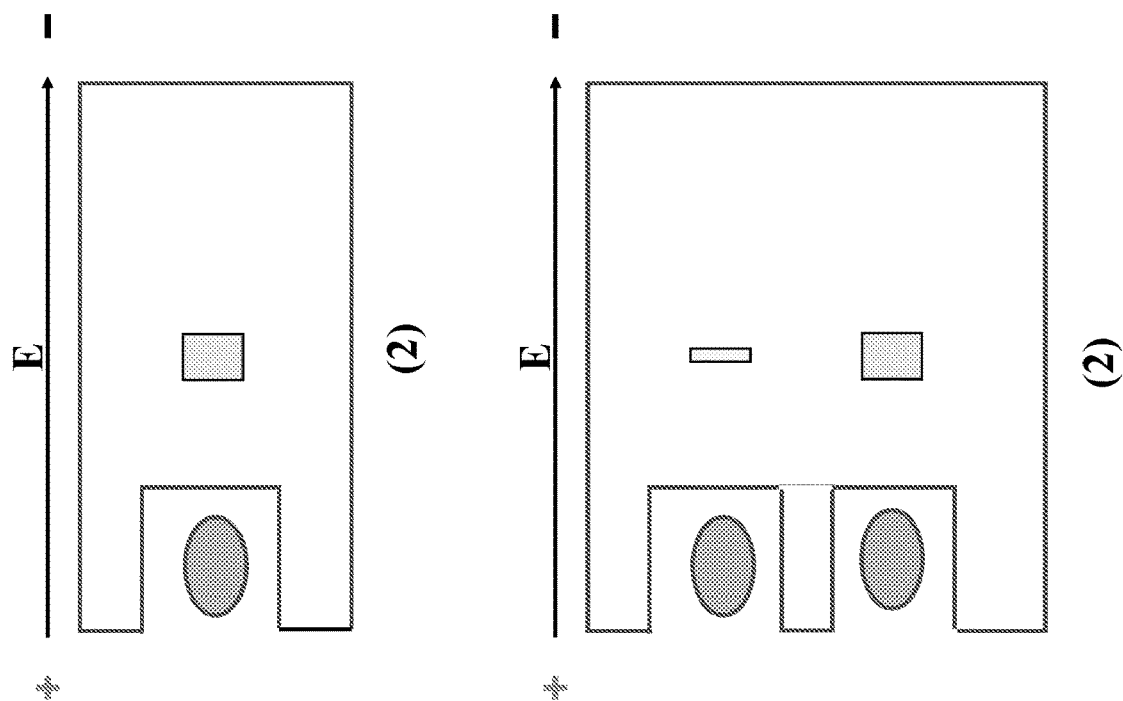
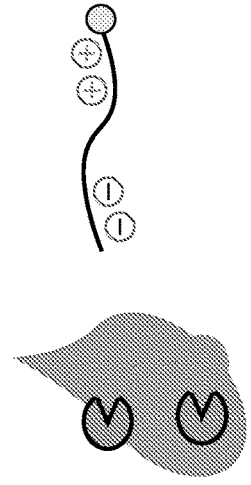
Fig. 7A
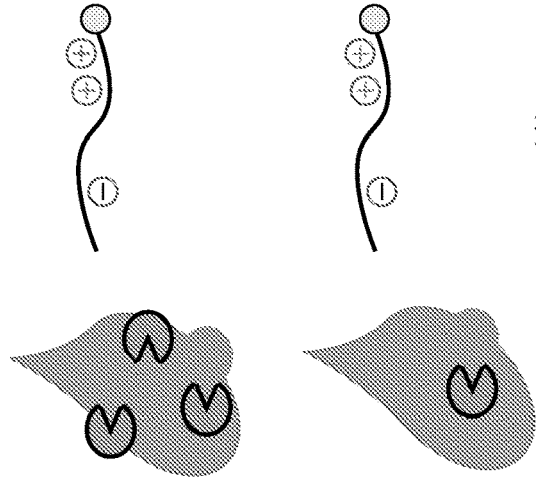
Fig. 7B

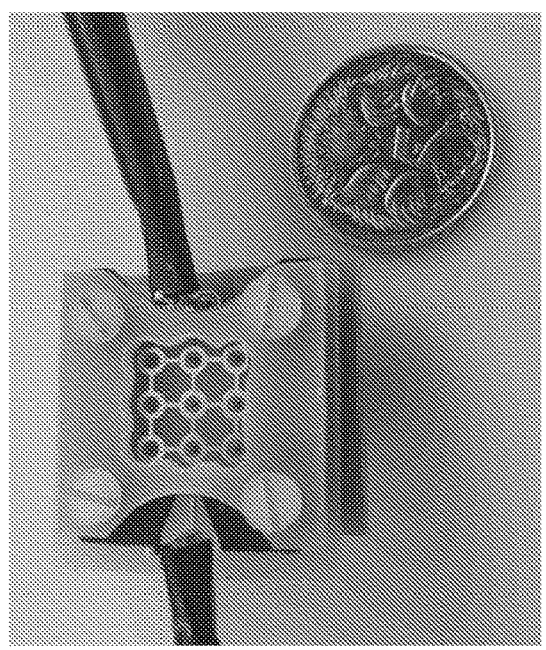
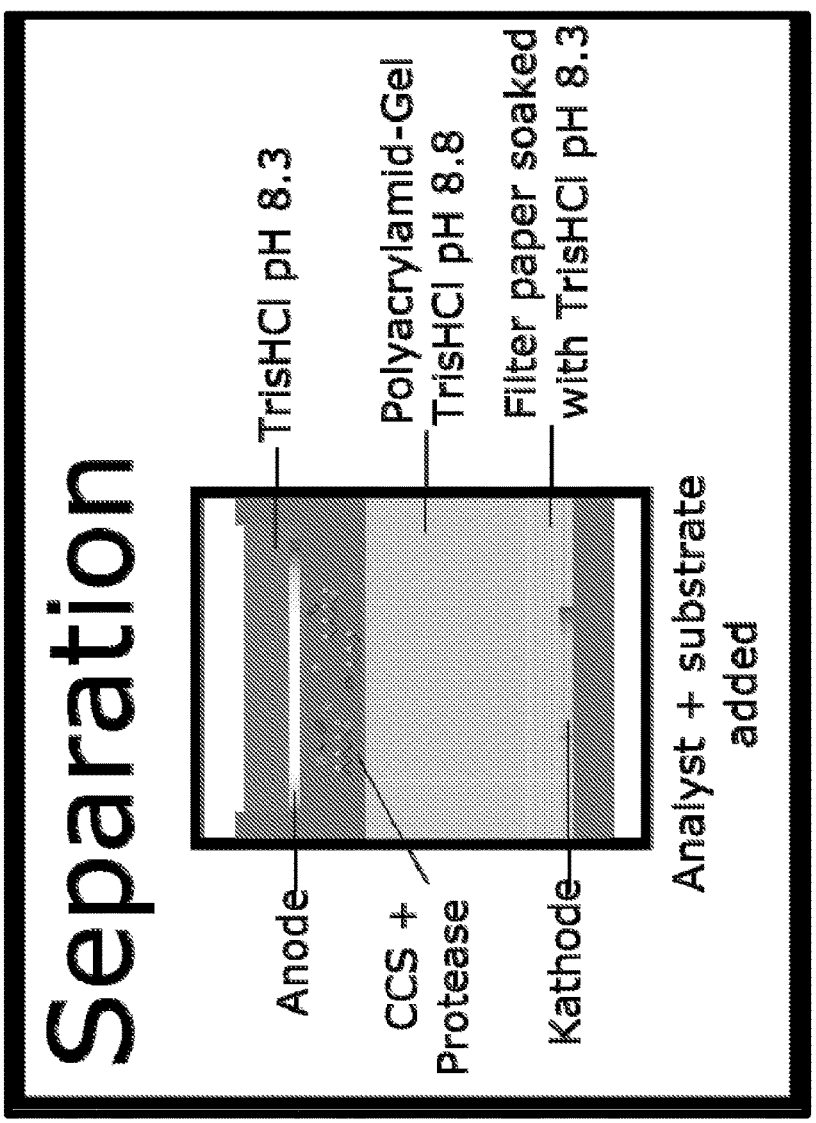
Fig. 8A

Coagulation Related Proteases:

Thrombin  Ac-N-D-D-Nle-T-P-R⁺//G-S-A-G-A-G-A-G-diamino-ethyl-BFL

Metalloproteases:

MMP1  Ac-N-D-G-P-Q-A//I-A-G-Q-G-A-G-diamino-ethyl-BFL
MMP3  Ac-D⁻-G-P-K⁺-P-V-E-//Nva-Y-N-K(ε-BFL)-NH₂
MMP8  Ac-N-D-G-P-Q-G//Y-A-G-Q-G-A-G-diamino-ethyl-BFL

Cathepsins:

Cathepsin-S  N-SUC-E-G-R⁺-W-H-T-V-G//L-R⁺-W-E-C(Cy5⁻)-R⁺-CO-NH₂
Cathepsin-D  N-SUC-D⁻-L-V-V-L//F-V-K⁺-K⁺-C(Cy5⁻)-A-CO-NH₂

Bacterial Proteases:

Omp-T  Ac-SUC-D⁻-G-D-K⁺-Y-R⁺//R⁺-A-W-G-D⁻T-I-diamino-ethyl-BFL
SspB   Ac-D⁻-G-D-A-F-S//K⁺-A-L-P-K(ε-BFL)-NH2

Kallikreins:

Kallikrein 3  Ac-N-D-G-S-S-I-Y//Q-S-S-T-G-diamino-ethyl-BFL
Kallikrein 2  Ac-N-D-G-D-T-F-R⁺//S-A-A-G-K(ε-BFL)-NH2

Calpains:

Calpain-1/2  N-SUC-E-P-L-F//A-A-R⁺-K(ε-BFL)-NH2

Fig. 9

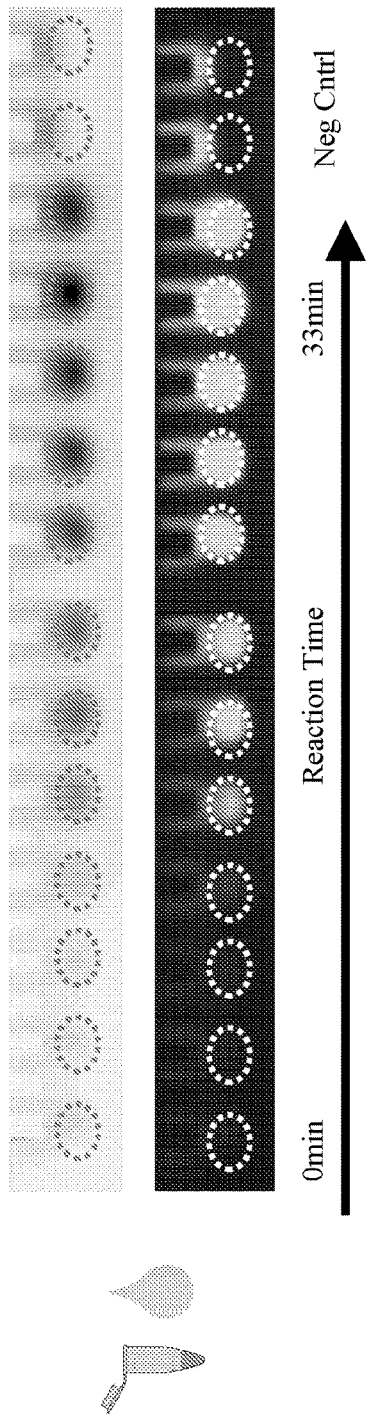
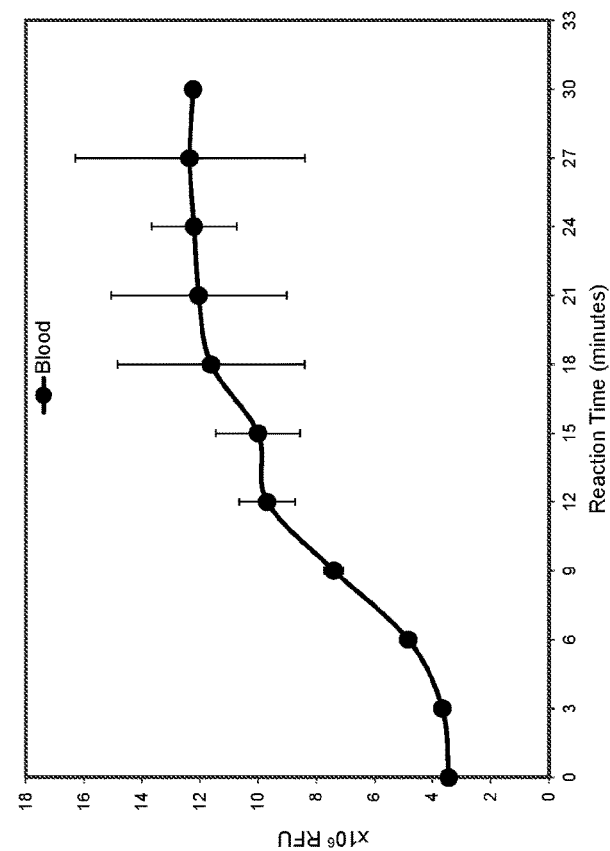
Fig. 11A
Fig. 11B

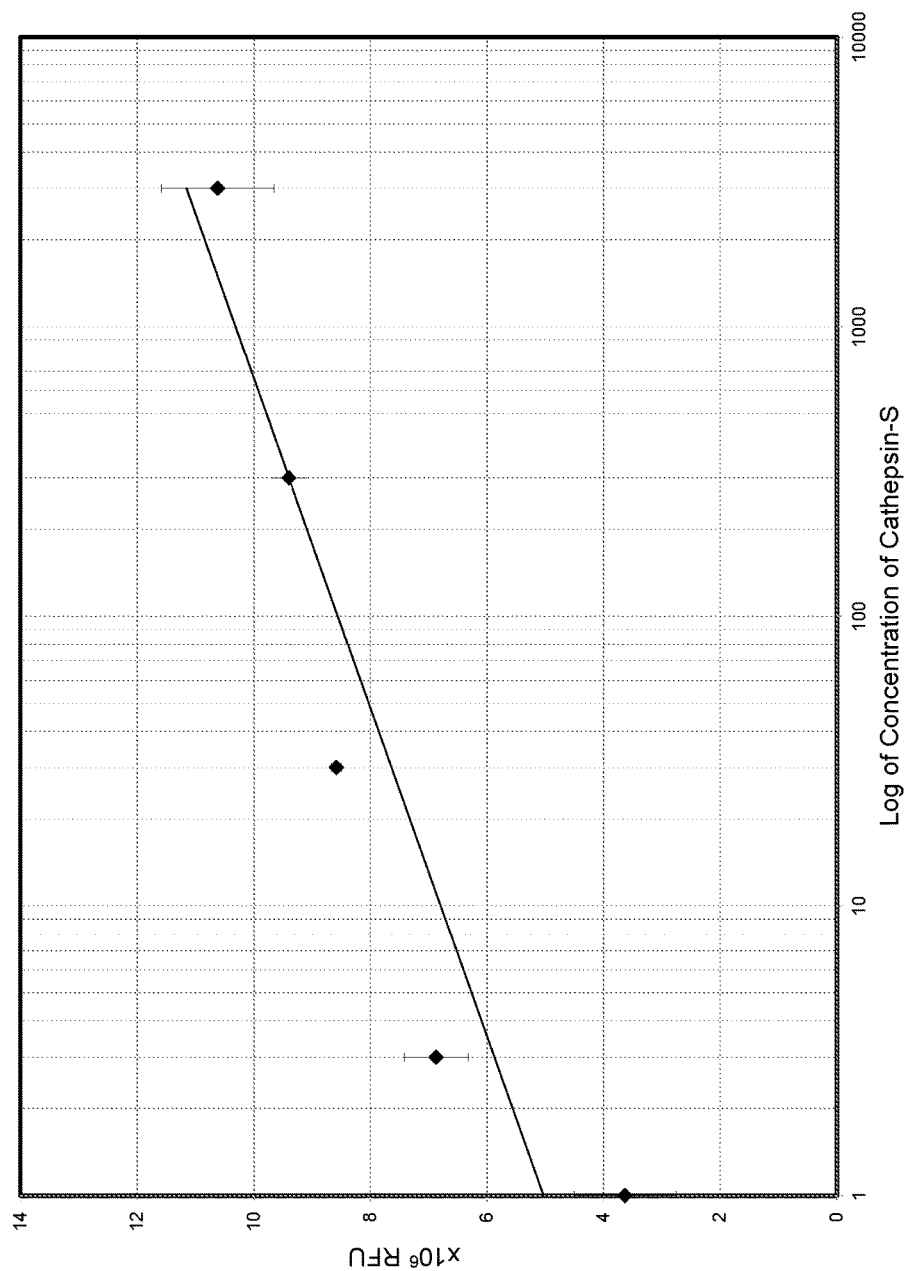
Fig. 12

DETECTION, IDENTIFICATION, AND PURIFICATION OF DEGRADATIVE AND NON-DEGRADATIVE ENZYMES IN BIOLOGICAL SAMPLES

CROSS-REFERENCE TO RELATED APPLICATIONS

This application is a 371 U.S. National Phase Application of PCT/US2017/056163, filed on Oct. 11, 2017, which claims priority to U.S. Provisional Application Ser. No. 62/406,781, filed Oct. 11, 2016, which is incorporated by reference in its entirety herein.

SEQUENCE LISTING

The instant application contains a Sequence Listing which has been submitted electronically in ASCII format and is hereby incorporated by reference in its entirety. Said ASCII copy, created on Apr. 22, 2021, is named 15670-0282US1_SL.txt and is 4,273 bytes in size.

TECHNICAL FIELD

This disclosure relates generally to methods of detecting protease activity in a complex biological sample, in particular methods of detecting degradative and non-degradative enzymatic activity in a complex biological sample, such as blood, plasma, or serum, without sample processing.

BACKGROUND

Over 300 protein post-translational modifications have been identified, and they profoundly influence protein function, localization, activity, and structure. Common post-translational modifications include phosphorylation, glycosylation, conjugation of small proteins such as ubiquitin and SUMO (small ubiquitin-related modifier), and acetylation of the N terminus and lysine residues, but the proteolytic modification of proteins is often overlooked in its importance and ubiquity. Indeed, many biomarkers of disease are stable proteolytic fragments in biological fluids.

Proteases are enzymes that carry out the hydrolysis of peptide bonds within proteins and polypeptides. Besides their roles in digestion and protein turnover, proteases function in tightly regulated cascades and signaling events. By precise proteolytic processing, proteases participate in every biological process including DNA replication and repair, cell cycle progression, cell proliferation, differentiation and migration, morphogenesis and tissue remodeling, neuronal outgrowth, hemostasis, wound healing, immunity, angiogenesis, and apoptosis. Indeed, more than 53 specific hereditary diseases of proteolysis are recognized, and it is not surprising then that proteases are implicated in many pathologies. In addition, numerous pathogens use proteases during the invasion of their host, for their replication inside the host, or in modulating the host's immune response.

For these reasons, proteases are considered important targets for therapeutic intervention. Proteases represent 5-10% of drug targets. With six classes of proteases that account for ~2% of the genes of any organism (see the peptidase database MEROPs for useful information), proteases constitute the second largest enzyme family in man after ubiquitin ligases, totaling more than 567 proteases. Several protease inhibitors have been developed into drugs against such diseases as HIV infection, multiple myeloma, and hypertension. Despite these successes, many protease inhibitors have failed in clinical trials due to a lack of selectivity or misconceptions about the functional role of the targeted protease(s).

These examples underscore the importance of having a better understanding of protease activity in a more complex and biologically relevant setting as part of the early drug discovery process, life sciences research, and diagnostics development.

SUMMARY

Provided herein are methods of detecting protease activity in a complex biological sample, in particular methods of detecting degradative and non-degradative enzymatic activity in a complex biological sample without sample processing. In some embodiments, the complex biological sample is selected from among blood, plasma, and serum.

Provided herein is a method of identifying protease activity in a complex biological sample, comprising: a) obtaining a complex biological sample; b) incubating the complex sample with a substrate library and a tag to generate cleavage products; c) separating the cleavage products from the complex sample; and d) generating a proteolytic signature for the complex sample.

In some embodiments of the method, the complex biological sample is whole blood.

In some embodiments of the method, the substrate library is a synthetic peptide library. In some embodiments, the synthetic peptide library comprises combinations of amino acid pairs, positively and negatively charged residues, or modified residues at different positions along the length of the synthetic peptides.

In some embodiments of the method, the cleavage products are separated from the complex sample by gel electrophoresis, capillary electrophoresis, or a combination of DC and AC electrokinetic techniques.

In some embodiments of the method, the substrate signature is generated by detecting and ranking individual substrates in the peptide mixture according to migration. In some embodiments, the individual substrates are detected via the tag. In some embodiments, the tag is a fluorescent dye, a radioactive probe, or an affinity tag.

In some embodiments of the method, the proteolytic signature comprises multiple classes of protease activity. In some embodiments, the multiple classes of protease activity are selected from serine, cysteine, threonine, aspartyl, and metallopeptidase activity. In some embodiments, the multiple classes of protease activity are detected by separately incubating the complex sample with an activity inhibitor. In some embodiments, the activity inhibitor is selected from a metal chelator, a cysteine peptidase inhibitor, and an elastase-specific inhibitor. In some embodiments, the activity inhibitor is selected from EDTA, E-64, CAO74, and a chloromethyl ketone inhibitor.

Provided herein is a method of purifying proteases in a biological sample, comprising: a) obtaining a biological sample; b) contacting the sample with an activity-based probe (ABP) comprising a chemically reactive group attached to a positively charged moiety, wherein the ABP binds to the active site of a protease in the biological sample and the positively charged moiety of the ABP remains exposed outside the active site of the protease; and c) separating the proteases that have bound ABP.

In some embodiments of the method, the chemically reactive group is attached to the positively charged moiety via a spacer molecule. In some embodiments of the method, the contacting occurs by incubating the ABP with the sample in vitro. In some embodiments, the chemically reactive group reacts irreversibly with the active site nucleophilic residue. In some embodiments, the proteases that have bound ABP are separated from the sample by electrophoretic separation Provided herein is a method of visualizing proteases in a biological sample, comprising: a) obtaining a biological sample; b) contacting the sample with an activity-based probe (ABP) comprising a chemically reactive group attached to a positively charged moiety, wherein the ABP binds to the active site of a protease in the biological sample and the positively charged moiety of the ABP remains exposed outside the active site of the protease; and c) visualizing the proteases that have bound ABP.

In some embodiments of the method, the contacting occurs by injecting the ABP in vivo. In some embodiments, the chemically reactive group is attached to the positively charged moiety via a spacer molecule. In some embodiments, the chemically reactive group reacts irreversibly with the active site nucleophilic residue. In some embodiments, the ABP further comprises a tag. In some embodiments, the tag is a fluorescent dye or a radioactive probe.

In some embodiments, the method further comprises performing a biopsy at the site of visualization. In some embodiments, the site of visualization is a tumor.

In some embodiments, the method further comprises separating the proteases that have bound ABP by electrophoretic separation.

Provided herein is a method of visualizing protease activity in an acidic microenvironment in vivo, the method comprising injecting a negatively charged fluorescently labeled peptide or nanoparticle into an organism, wherein the peptide or nanoparticle enters an acidic microenvironment and is cleaved by a protease in the microenvironment to generate a positively charged fluorescent cleavage product; and visualizing the cleavage product.

In some embodiments of the method, the acidic microenvironment is in a tumor. In some embodiments, the cleavage product sticks to the cell surface of the tumor.

Provided herein is a method of detecting amphiphilic enzyme substrates in a complex biological sample by contact angle measurement, comprising: a) incubating a droplet of a complex biological sample with an amphiphilic substrate that balances hydrophobicity and hydrophilicity around a protease cleavage site, wherein hydrophilic and hydrophobic products are released from the amphiphilic substrate; and b) measuring the contact angle that forms as the hydrophobic cleavage products migrate to the surface of the droplet-air interface at the surface of the droplet, wherein a decrease in contact angle indicates protease activity.

Provided herein is a method of detecting amphiphilic enzyme substrates in a complex biological sample by fluorescence, comprising: a) incubating a droplet of a complex biological sample with a fluorescently labeled amphiphilic substrate that balances hydrophobicity and hydrophilicity around a protease cleavage site, wherein hydrophilic and hydrophobic products are released from the amphiphilic substrate; and b) measuring the fluorescence of the hydrophobic cleavage products that migrate to the surface of the droplet-air interface at the surface of the droplet, fluorescence indicates protease activity.

Provided herein is a method of detecting non-degradative, charge-transferring enzymes in a biological sample, comprising incubating positively charged substrates with complex samples designed to become negatively charged upon phosphorylation by kinases in the sample and measuring the fluorescence in an electrophoresis gel.

In some embodiments of the method, the substrates comprise residues selected from serine, threonine, tyrosine, and combinations thereof.

DESCRIPTION OF DRAWINGS

FIGS. 1A-1B show the use of substrate libraries and the resulting patterns of substrate cleavage to identify enzymes in a sample. FIG. 1A illustrates the use of non-targeted libraries of substrates and the resulting patterns of substrate cleavage to identify multiple enzymes in samples. FIG. 1B illustrates substrate panels and resulting patterns of substrate cleavage to differentiate enzymes with overlapping cleavage specificities such as MMP-2 (top panel) and MMP-9 (bottom panel).

FIG. 2A shows a protease inhibitor molecule with a negatively charged inhibiting region and a positively charged tail. FIG. 2B shows that the protease binds the inhibitor molecule and masks the negatively charged inhibiting region while the tail remains exposed with positive charge, but does not cleave the molecule. FIG. 2C shows application of an electric field to the sample to separate the negatively charged blood components from the positively charged protease/inhibitor. FIG. 2D shows that the method is used to screen inhibitor molecules in complex samples by separating all inhibited proteases and characterizing for off-target proteases.

FIG. 3A shows injection of a FRET peptide into an animal that is negatively-charged to provide better transport in the bloodstream. FIG. 3B shows that upon reaching the tumor microenvironment, the acidity of the tumor microenvironment protonates histidine, rendering the peptide neutral and able to penetrate into the tumor. FIG. 3C shows the peptide, designed to be cleaved by proteases associated with the tumor microenvironment, is cleaved and unquenched. FIG. 3D shows that the positively charged cleavage product is "sticky" to the cell surface. Fluorescent signal indicates tumor protease activity and tumor protease localization.

FIGS. 4A-4E show 3-step charge-changing substrates that enhance protease detection, imaging, and payload delivery in acidic microenvironments of tumors. FIG. 4A shows a peptide designed to contain a cleavage site for a protease associated with cancer that is displayed at the cancer cell surface. The peptide is designed to change charge with tumor-associated pH change and cancer cell surface-associated proteolytic cleavage to enhance nanoparticle (NP) delivery. FIG. 4B shows the negatively charged NP in the bloodstream for stealth in circulation. FIG. 4C shows the NP is neutral in the acidic tumor microenvironment and remains slippery to diffuse deep into the tumor. FIG. 4D shows a protease at the cancer cell surface cleaving the peptide at the NP surface, leaving the NP positively charged for sticky cell binding. FIG. 4E shows a positively charged NP sticks to cancer cell membranes and is electrostatically adsorbed, triggering cellular uptake.

FIGS. 5A-5B illustrate detection of amphiphilic enzyme substrates. FIG. 5A shows the contact angle of sample droplet indicates protease activity yielding hydrophobic products. (1) The sample is incubated with a substrate that balances hydrophobicity and hydrophilicity around a protease cleavage site; (2) proteases cleave substrates, producing hydrophilic and hydrophobic products; and (3) hydrophobic products migrate to the air/liquid interface and reduce the contact angle of the sample droplet, indicating proteolytic activity. FIG. 5B shows the fluorescent hydrophobic cleavage products assemble at surface of droplet where fluorescence is not quenched by components of droplet. (1) The sample is incubated with a substrate that balances hydrophobicity and hydrophilicity around a protease cleavage site; (2) proteases cleave substrates, producing hydrophilic and hydrophobic products; and (3) hydrophobic products migrate to the air/liquid interface and fluorescence is displayed on the surface of the droplet, indicating proteolytic activity.

FIGS. 7A-7B shows the detection of non-degradative enzymes such as phosphorylases and kinases using charge-changing substrates and electrophoretic separation from unprocessed sample. FIG. 7A shows (1) a phosphorylase removing negatively charged phosphate groups from a substrate, such as a phosphorylated serine group and (2) electrophoretic separation of the positively charged dephosphorylated substrate. FIG. 7B shows (1) kinases adding a negatively charged phosphate group to a substrate and (2) comparison between samples with kinase activity of negatively charged phosphorylate substrate that has reduced fluorescence.

FIGS. 8A-8B show an electrophoresis focusing assay.

FIG. 9 shows charge-changing peptide sequences that selectively target proteases that include coagulation related proteases (thrombin), metalloproteases (MMP1, MMP3, and MMP8), cathepsins (cathepsin-S and cathepsin-D), bacterial proteases (Omp-T and SspB), kallikreins (kallikrein 2 and kallikrein 3), and calpains (calpain 1 and calpain 2).

FIG. 10A shows incubation of thrombin and the peptide substrate in 1×PBS. FIG. 10B is a graph showing thrombin concentration after incubation in 1×PBS. FIG. 10C shows incubation of thrombin and the peptide substrate in citrated blood. FIG. 10D is a graph showing thrombin concentration after incubation in citrated blood.

FIGS. 11A-11B show whole blood thrombin detection using a thrombin-specific charge-changing peptide substrate. FIG. 11A illustrates fluorescence signal at various incubation time points. As compared to a negative control. FIG. 11B is a graph showing fluorescence intensity at various incubation time points.

FIG. 12 shows cathepsin-S in buffer (1×PBS) detection using a cathepsin-S specific charge-changing fluorescent substrate.

FIG. 13A shows fluorescence after time in control subjects (top panel) vs. anticoagulant subjects (bottom panel). FIG. 13B is a graph showing thrombin activity over time.

FIG. 14C shows that thrombin activity can be monitored in real time.

FIG. 15A shows a miniaturized array prototype. FIG. 15B shows the results of an electrophoresis focusing assay measuring protease (trypsin) activity as fluorescence intensity vs. concentration.

FIG. 16A shows a miniaturized array prototype. FIG. 16B shows the results of an electrophoresis focusing assay measuring protease (trypsin) activity after one week as fluorescence intensity vs. concentration.

FIG. 17A shows a miniaturized array prototype. FIG. 17B shows the results of an electrophoresis focusing assay measuring protease (trypsin) activity in a blood sample as fluorescence intensity vs. concentration.

DETAILED DESCRIPTION

Figure 1B:
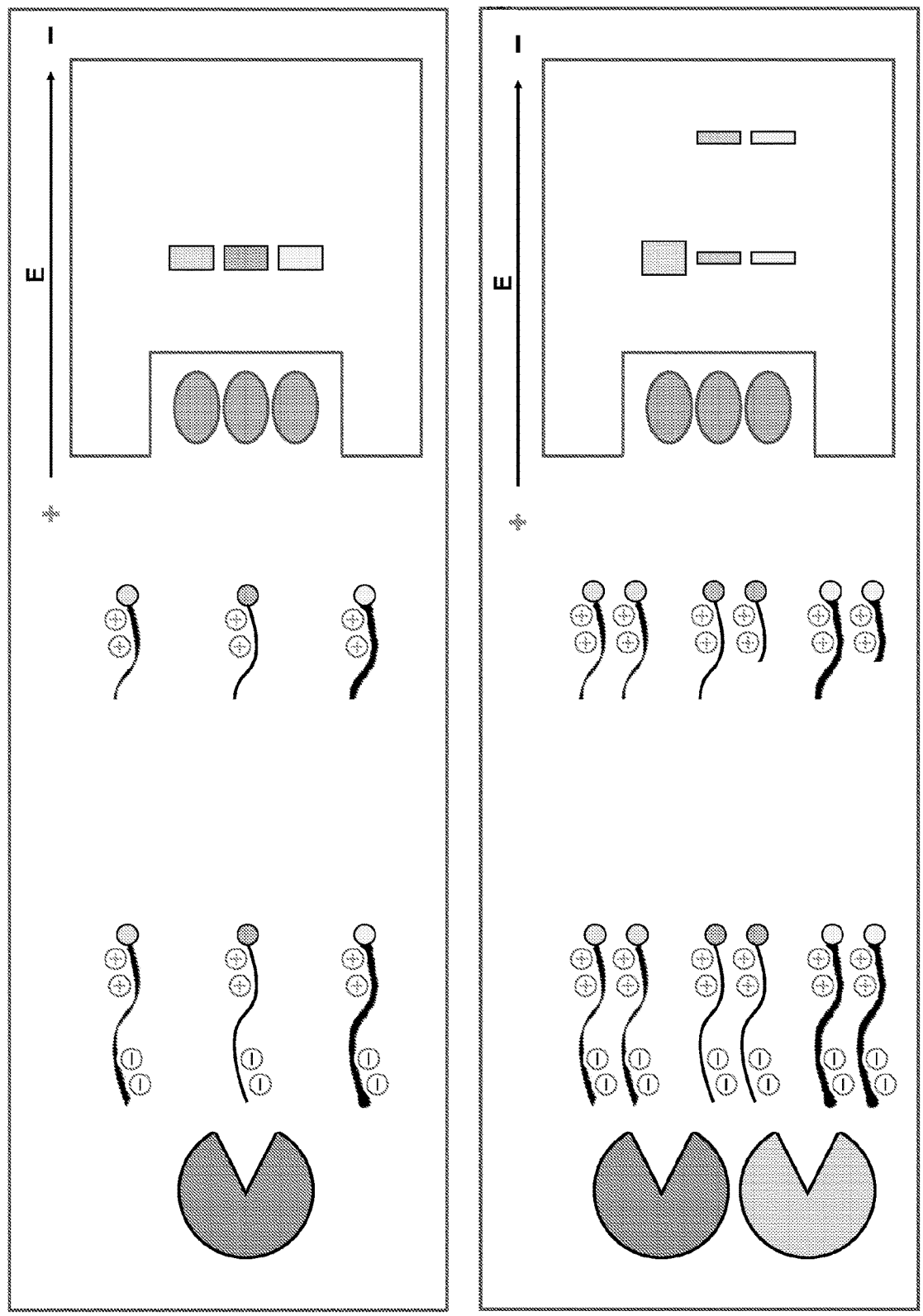
Figure 2A:
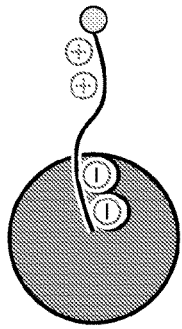
FIGS. 2A-2D show activity-based probes with charged moieties for protease purification.
Figure 2B:
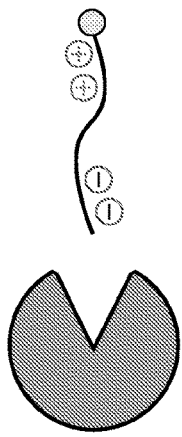
Figure 2C:
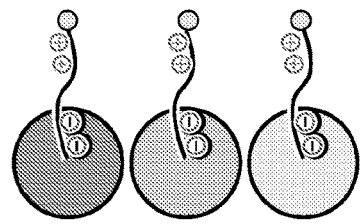
Figure 2D:
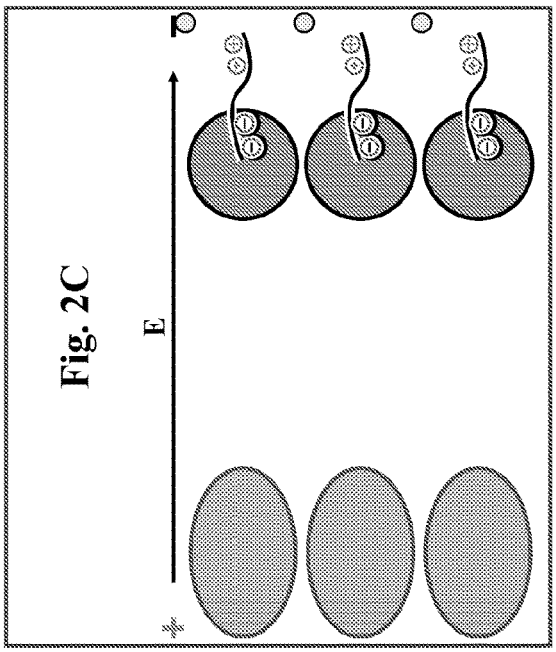
Figure 3A:
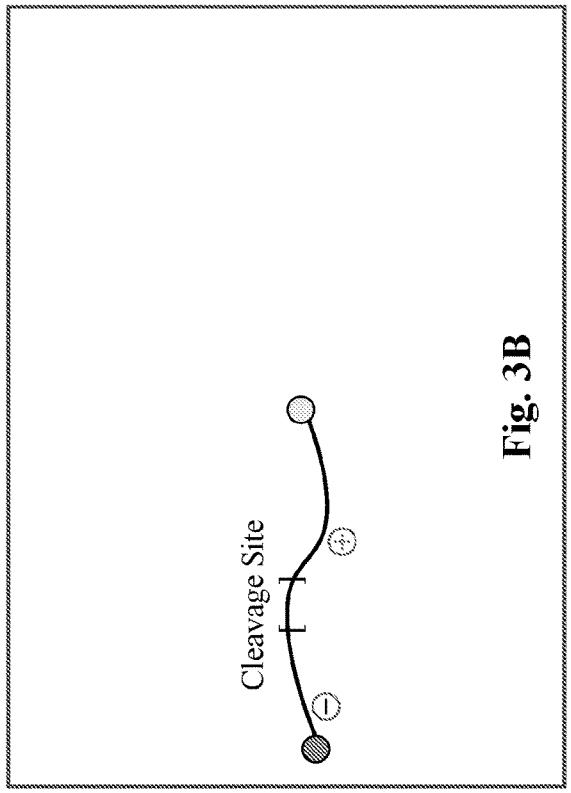
FIGS. 3A-3D show in vivo imaging of protease activity and localization using charge-changing substrates.
Figure 3B:
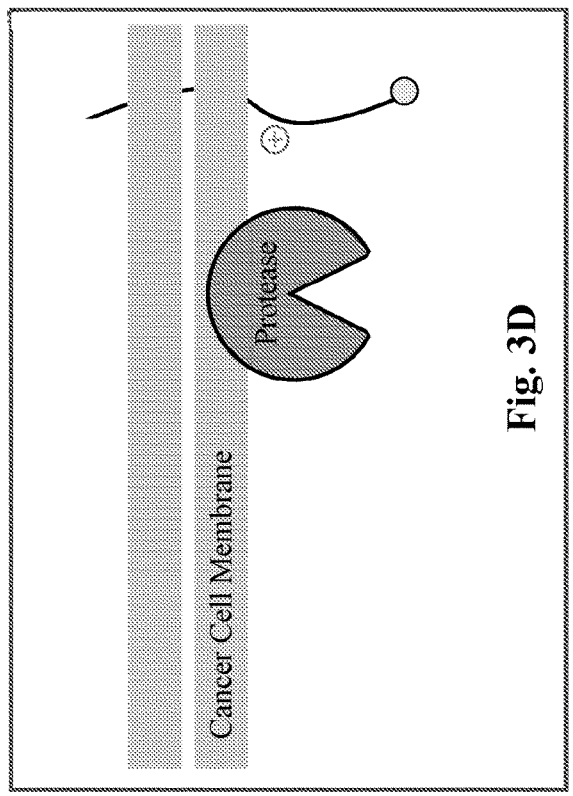
Figure 3C:
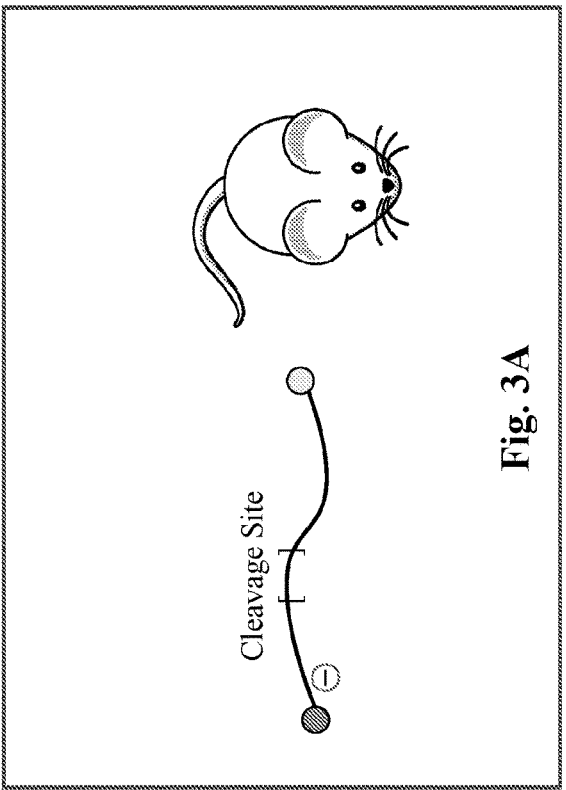
Figure 3D:
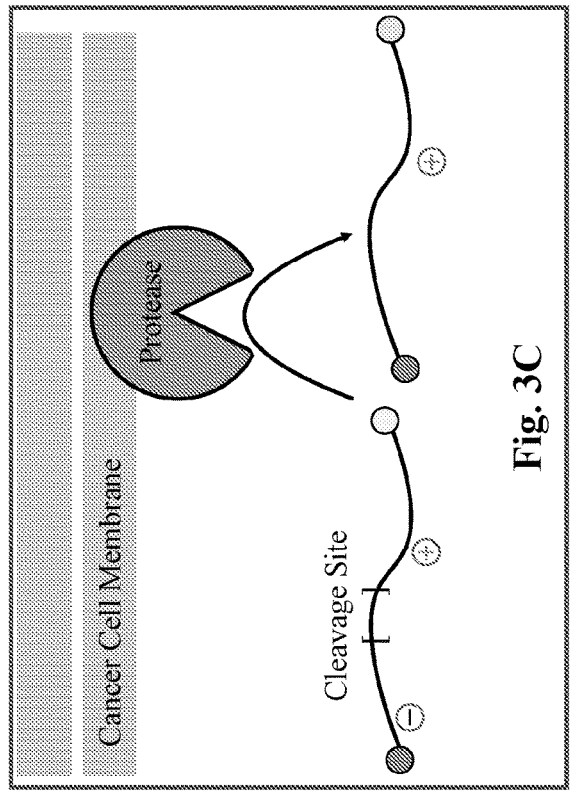

Provided herein are methods of detecting degradative and non-degradative enzymatic activity in complex biological samples without sample processing. In some embodiments, targeted or non-targeted libraries of property-changing (e.g., charge, hydrophobicity) enzyme substrates are separated from the biological sample based on their change in properties upon enzymatic action, for example, cleavage or moiety addition/subtraction. In some embodiments, separation of property-changing (e.g., charge, hydrophobicity) enzyme substrates is by electro kinetic methods, chromatographic techniques, and in situ assembly at hydrophobic-hydrophilic, e.g. air-liquid, interfaces. In some embodiments, detection of cleavage products of charge-changing and hydrophobicity-changing enzyme substrates is done using fluorescent/colorimetric dyes, impedance/capacitance detectors, contact angle, and turbidity/light absorption measurement to indicate enzymatic activity in complex samples. In some embodiments, the complex biological sample is selected from among blood, plasma, and serum. In some embodiments, formats including non-targeted library platforms, 96-well plates, lateral flow assays, cassettes, skin patches, and microarrays adapted for separation based on charge/hydrophobicity changes are used.

Also provided herein are methods of enabling the purification of enzymes, e.g. proteases, from complex samples without sample processing. In some embodiments, the complex biological sample is selected from among blood, plasma, and serum. In some embodiments, charge-balanced probes that inhibit/bind the cleavage/allosteric site of the enzyme through their negatively charged section are used. In some embodiments, the enzyme shields this bound negatively charged section of the probe while the positively charged section of the probe is not shielded and used to separate out the enzyme from the complex sample under the action of an electric field. In some embodiments, the complex biological sample is selected from among blood, plasma, and serum.

In some embodiments, an assay technique is used to detect and measure proteases directly in a few microliters of whole blood. In some embodiments, the protease is selected from among indigenous and nonindigenous proteases including, but not limited to trypsin, chymotrypsin, MMPs, and combinations thereof. In some embodiments, the protease is thrombin. Many indigenous proteases like thrombin are important for blood clotting activities and related cardiac diseases (DVT, atherosclerosis, etc.). The appearance of certain nonindigenous proteases like trypsin, chymotrypsin, and MMPs are frequently biomarkers for shock, cancer and other diseases. Thus, the ability to measure protease activity in whole blood will allow researchers to further elucidate the relationship between circulating protease levels and many important diseases.

Provided herein are synthetic charge-changing fluorescent peptide substrates which are specific for proteases. In some embodiments, the protease is selected from trypsin, chymotrypsin, MMP2, MMP9, elastase, and thrombin. In some embodiments, the peptide substrates allow direct detection of protease activity in a complex biological sample and eliminate the need for sample preparation. In some embodiments, the complex biological sample is selected from among blood, plasma, and serum. In some embodiments, the substrates are added to a few microliters of a complex sample for reaction, and the cleaved products are then rapidly separated in a simple electrophoretic microgel format. In some embodiments, the complex samples is blood.

In some embodiments, the target of the invention are catalytic enzymes, including, but not limited to proteases, lipases, nucleases, and non-catalytic enzymes. In some embodiments, the targets are proteases.

In some embodiments of the assays and methods provided herein, the sample to be analyzed is a biological sample. In some embodiments, the input material is a biological sample such as blood, saliva, cerebro-spinal fluid, or urine. In some embodiments, the biological sample is blood. In some embodiments, the sample does not require special processing before being placed into the process.

In some embodiments, the assays and methods provided herein can be performed in laboratory ware. In some embodiments, the laboratory ware includes a 96-well pate or flask, a reaction container such as a cassette, or a lateral flow device similar to a pregnancy test kit, etc. In some embodiments, a patch-type device for placing on a person that allows for continuous monitoring is also considered.

In some embodiments, the reacting elements are chemicals. In some embodiments, the reacting elements include, but are not limited to, synthesized sequences of peptides, DNA, and RNA. In some embodiments, the chemicals carry 'tags' to facilitate the process. In some embodiments, the chemicals are engineered to bear hydrophilic and hydrophobic regions, or positively and negatively charged regions, although other differentiating features could be chosen. In some embodiments there is a single chemical used in the process. In some embodiments there is a plurality of chemicals, where such plurality can be chosen for a unique combination of reaction outputs. These plurality of chemicals would comprise a 'library' of available molecules for use.

In some embodiments the tags are fluorescent. In some embodiments, the tags are luminescent or radioactive. In some embodiments, the tag includes a sequence that is dominated by entities bearing specific physio-chemical properties, such as charge or hydro-phobicity/philicity.

In some embodiments of the assays and methods provided herein, the reaction that occurs is a chemical reaction. In some embodiments, the chemical reaction is proteolytic activity by the enzymes present in the biological sample digesting/degrading the tag-bearing-chemicals. In some embodiments, the chemical reaction is binding or another reaction. The tag-bearing chemicals function as substrates for the enzymes, or as protease-specific peptides. In some embodiments, the reaction cleaves the peptides, releasing a hydrophobic, or highly-charged, or otherwise 'polarized' entity. Such an entity possesses properties that can be separated and measured, for useful purposes. Alternatively, in some embodiments, the tag-bearing chemicals function to bind a region or pocket of the enzyme in the sample, where such binding exposes only one portion of the chemical, where such exposure allows a method of separation and measurement.

In some embodiments, following the reaction, a processing step can occur. In some embodiments, the processing step is an electrophoretic process, chromatography, lateral flow, or hydrophobic moieties moving to the surface of the liquid, etc. This can be a single step, or several steps. In some embodiments, this processing can also include purification or extraction of enzymes of interest.

In some embodiments, following the processing, measurement can be performed. In some embodiments, the measurement is electrical, conductivity, impedance, or colorimetric. In some embodiments, the measurement is interpreted by an operator, or by software, that enables a useful result, such as a diagnostic output, to be rendered.

Protease Activity Profiling with Libraries of Charge-Changing Peptides

Functional characterization of peptidases in a biological system has traditionally involved identifying a candidate protein, determining the substrate specificity and generating a specific probe or inhibitor. Although the candidate approach has a proven track record, there is a need to characterize proteolysis using an unbiased global approach. Recently two DNA microarray technologies, the Hu/Mu ProtIn chip and the CLIP-CHIP®, were developed to study proteases. However, transcript levels only indicate which proteases can potentially be found in a sample because mRNA levels do not always correlate with protein abundance and are devoid of information regarding protease activity. Proteomics offers a means to evaluate the presence of proteins and their changes in abundance within complex mixtures. However, it also fails to detect the functional state of a protein. For proteases there is a difference between abundance and activity, and a technique to track protease activity in complex samples is needed.

To study this, the concept of "reverse degradomics" was introduced, which seeks to measure the total impact of a complex biological sample on a particular substrate. Fluorescently labeled substrates are incubated with biological samples, and at different time points the degree of degradation is assessed in a high-throughput manner. This enables one to predict and compare the total impact of complex samples on, for example, key disease-related substrates, in a setting close to the in vivo substrate environment. However, these reverse techniques, including zymography and mass spectrometry, rely on time consuming protocols, highly specialized equipment, and manipulation of samples by processing.

Identifying the Proteolytic Signature of Complex Samples

Provided herein are methods of identifying the proteolytic signature of complex samples. In some embodiments, the complex biological sample is selected from among blood, plasma, and serum. In some embodiments, provided herein is a method of generating comprehensive substrate signatures for enzyme classes in complex samples. In some embodiments, the substrate library and the resulting pattern of substrate cleavage is used to identify enzymes in a sample. For example, a synthetic peptide library containing combinations of amino acid pairs, combinations of positively and negatively charged residues or modified residues at different positions along the length of the synthetic peptides, and a tag such as a fluorescent dye can be prepared. In some embodiments, substrate signatures can be generated after an incubation of complex samples with the substrate library and separation of the cleavage products of the incubated substrate library from the complex sample by gel electrophoresis, capillary electrophoresis, or a combination of DC and AC electrokinetic techniques (FIGS. 1A-1B). In some embodiments, individual substrates in the peptide mixture are ranked according to migration and detected via fluorescence or other tag. In some embodiments, enzymes with overlapping cleavage specificities can be differentiated. For example, in some embodiments, MMP-2 and MMP-9 can be differentiated.

In some embodiments, to dissect the contribution of multiple classes of protease activity such as serine, cysteine, and metallopeptidases, samples are tested after being incubated separately with various activity inhibitors. In some embodiments, the activity inhibitors are the metal chelator EDTA, the cysteine peptidase inhibitors E-64 and CAO74, or the elastase-specific chloromethyl ketone inhibitor. In some embodiments, cleavage-site specificity data from inhibited samples is combined to generate a substrate signature for each peptidase class. In some embodiments, secondary synthetic peptide libraries are generated to further define the cleavage preferences of peptidases in complex samples. In some embodiments, the complex biological sample is selected from among blood, plasma, and serum.

Protease Purification with Charge-Changing Activity-Based Probes

Identification and quantification of active proteases found in biological samples can be achieved by combining the use of activity-based probes (ABPs) and mass spectrometry analysis. ABPs are molecules derived from mechanism-based inhibitors. ABPs have been developed for several enzyme classes, but have proven particularly useful for the study of proteases. ABPs targeting serine proteases, cysteine proteases, threonine proteases, aspartyl proteases, and metalloproteases have been developed. ABPs irreversibly bind to active proteases but not to inactive zymogens or an inhibited enzyme. ABPs are composed of a chemically reactive group, often termed a "warhead," attached to a tag moiety via a spacer molecule. Selectivity of the probe can be increased by the addition of a specificity-enhancing module. Upon binding of the ABP to the protease active site, the chemically reactive group reacts irreversibly with the active site nucleophilic residue. The tag of ABPs allows for either visualization (fluorophore or radioactive probe) or isolation (affinity tag) of the ABP.protease complex.

However, ABP approaches rely on time consuming protocols, highly specialized equipment, and manipulation of samples by processing. There is a need for techniques that enable unamplified study of protease activity, as is accomplished with ABP as opposed to cleavable substrate methods, that also function in complex samples and do not require specialized equipment such as mass spectrometry. In some embodiments, the complex biological sample is selected from among blood, plasma, and serum.

In Vitro/In Vivo Purification by Activity Based Probes

In some embodiments, provided herein are activity-based probes with charged moieties for protease purification. In some embodiments, provided is an ABP design composed of a chemically reactive group attached to a positively charged moiety via a spacer molecule (FIGS. 2A-2D). In some embodiments, the protease inhibitor molecule has a negatively charged inhibiting region and a positively charged tail. In some embodiments, the ABP is incubated with a sample in vitro or injected in vivo. In some embodiments, the ABP binds to the protease active site and the chemically reactive group reacts irreversibly with the active site nucleophilic residue. In some embodiments, the protease binds the inhibitor molecule but does not cleave the molecule. In some embodiments, the protease binds the inhibitor molecule and masks the negatively charged inhibiting region. In some embodiments, the positively charged moiety of the ABP (e.g., tail) remains exposed outside the active site of the protease.

In some embodiments, electrophoretic separation in vitro is used to separate the proteases that have bound ABP since the positively charged moiety will separate from the majority of components of the complex biological sample that are negatively charged. In some embodiments, the complex biological sample is selected from among blood, plasma, and serum. In some embodiments, an electric field is applied to the sample. In some embodiments, the negatively charged blood components separate from the positively charged protease/inhibitor.

In some embodiments, following in vivo injection of an ABP with a positively charged moiety and an identifying tag such as a near-infrared or fluorescent dye, visualization of protease activity is possible. In some embodiments, visualization of protease activity at the site of a tumor is possible. In some embodiments, the tumor is biopsied. In some embodiments, after biopsy the ABP-bound proteases are separated from the complex sample by electrophoretic separation. In some embodiments, ABP-bound proteases that have been separated from complex samples are available for further downstream applications and characterization of post-translational modifications, mutations, etc. In some embodiments, the complex biological sample is selected from among blood, plasma, and serum.

Protease Detection and Imaging of Acidic Microenvironments In Vivo

The introduction of whole-body imaging techniques for small animals enabled in vivo zymography (IVZ). This technique relies on the use of protease-activated fluorogenic probes. Specific probes have been developed containing different fluorophores, which allow simultaneous detection of various enzymes. IVZ has allowed the mapping of MMP activity patterns in an intact organism. However, IVZ probes are not designed to preferentially localize in certain microenvironments of the body, which could afford more accurate imaging of hard to access microenvironments of interest, such as the acidic microenvironments of tumors.

In Vivo Protease Detection by Peptides

In some embodiments, provided are methods of imaging protease activity and localization using charge-changing substrates. In some embodiments, the imaging is in vivo. In some embodiments, the protease detection technique enables in vivo imaging of localized protease activity in acidic microenvironments based on charge-changing fluorescent probes (FIGS. 3A-3D). In some embodiments, a negatively charged fluorescently labeled peptide is injected into an organism. In some embodiments, the peptide is a FRET peptide. In some embodiments, the negative charge of the peptide affords stealth in the bloodstream of the organism. In some embodiments, upon encountering the acidic microenvironment of a tumor, the histidine residues of the peptide become positively charged and the peptide is overall neutral. In some embodiments, the peptide is rendered neutral and able to penetrate the tumor. In some embodiments, the neutral charge allows the peptide to penetrate the tumor. In some embodiments, the peptide is cleaved by the protease for which its sequence was designed. In some embodiments, the peptide is designed to be cleaved by proteases associated with the tumor microenvironment. In some embodiments, the peptide is cleaved and unquenched. In some embodiments, the cleavage product is positively charged and fluorescently or near infrared labeled which causes it to stick to the cell surface and provide imaging of protease activity and localization. In some embodiments, a fluorescent signal indicates tumor protease activity and tumor protease localization.

Surface charge of nanocarriers influences their penetration into tumor tissues. The extracellular matrix presents as an effective electrostatic bandpass, suppressing the diffusive motion of both positively and negatively charge objects, which allows uncharged particles to easily diffuse through while effectively trapping charged particles. The optimal particles for delivery to tumors should be neutral after exiting the blood vessels (see, e.g., Sun Q, Radosz M, Shen Y, Chapter 3: Rational Design of Translational Nanocarriers. Functional Polymers for Nanomedicine, edited by Younqing Shen).

To deliver a sufficient drug concentration to the tumor center region lacking vascular perfusion, where the most aggressive and resistant cells reside, the nanocarrier should not release the carried drug after extravasation but should further diffuse deep into the tumor. This requires the nanocarrier to remain slippery and have as small a size as possible. Thus, it is better for the nanocarrier to be neutral and not to present any binding groups (including targeting groups) until reaching the center of the tumor.

After reaching the targeted region the nanocarrier should efficiently enter the cells for drug release. Now the same properties that impart stealth to the nanocarrier prevent it from cellular uptake by tumor cells. Nanocarriers that are negatively charged will be repelled from the cell membrane due to the electrostatic repulsion. Thus, once in the tumor, the carrier must become cell-binding or sticky to targeting tumor cells for fast cellular uptake. The challenge is how to reconcile these two opposite requirements, stealth for circulation and diffusion versus sticky for targeting. For instance, it is well known that positively charged carrier reliably stick to cell membranes due to electrostatic adsorption triggering fast cellular uptake, but positively charged carriers are not suitable for in vivo applications because they are systemically toxic and have short circulation time (see, e.g., Sun Q, Radosz M, Shen Y, Chapter 3: Rational Design of Translational Nanocarriers. Functional Polymers for Nanomedicine, edited by Younqing Shen).

Positive charges can promote carrier adsorption on the negatively charged membrane and hence trigger adsorption-mediated endocytosis. Thus, an alternative is to use tumor extracellular acidity to impart positive charges to the carrier by a "charge-reversal" technique.

In Vivo Protease Detection by Peptide Decorated Nanoparticles

In some embodiments, provided is a method of detecting protease activity in vivo using peptide-decorated nanoparticles. In some embodiments, provided is a protease detection technique that enables in vivo imaging of localized protease activity in acidic microenvironments. In some embodiments, the method uses nanoparticles decorated with charge-changing probes (FIGS. 4A-4E). In some embodiments, the peptide is designed to contain a cleavage site for a protease associated with cancer. In some embodiments, the protease associated with cancer is displayed at the cancer cell surface. In some embodiments, the peptide is designed to change charge with a tumor-associated pH change. In some embodiments, the peptide is designed to change charge with cancer cell surface-associated proteolytic cleavage. In some embodiments, the charge change and cleavage enhance nanoparticle delivery.

In some embodiments of the methods provided herein, a nanoparticle decorated with negatively charged peptides is injected into an organism. In some embodiments, the negative charge of the peptide affords stealth in the bloodstream of the organism. In some embodiments, upon encountering the acidic microenvironment of a tumor, the histidine residues of the peptide become positively charged and the peptide is overall neutral, which allows the decorated nanoparticle to penetrate the tumor. In some embodiments, the peptide on the surface of the nanoparticle is cleaved by the protease for which its sequence was designed. In some embodiments, the cleavage product is positively charged which causes the decorated nanoparticle to stick to the cell surface. In some embodiments, the positively charged nanoparticle is electrostatically adsorbed and triggers cellular uptake. In some embodiments, the nanoparticle releases its payload of imaging agents and/or drug molecules into the tumor cell.

In some embodiments of the methods provided herein, the charge-changing substrates enhance protease detection. In some embodiments of the methods provided herein, the charge-changing substrates enhance protease imaging. In some embodiments of the methods provided herein, the charge-changing substrates enhance payload delivery in acidic microenvironments of tumors.

In some embodiments of the methods provided herein, the charge-changing peptide sequences selectively target proteases selected from among coagulation related proteases, serine proteases, metalloproteases, cathepsins, bacterial proteases, kallikreins, and calpains (FIG. 9). In some embodiments, the coagulation related protease is thrombin and the charge-changing peptide sequence has the sequence Ac-N-D$^-$-D$^-$-Nle-T-P-R$^+$//G-S-A-G-A-G-A-G-diamino-ethyl-BFL (SEQ ID NO:1). In some embodiments, the serine protease is trypsin. In some embodiments, the metalloprotease is selected from among MMP1, MMP2, MMP3, MMP8, and MMP9. In some embodiments, the metalloprotease is MMP1 and the charge-changing peptide sequence has the sequence Ac-N-D$^-$-G-P-Q-API-A-G-Q-G-A-G-diamino-ethyl-BFL (SEQ ID NO:2). In some embodiments, the metalloprotease is MMP2. In some embodiments, the metalloprotease is MMP3 and the charge-changing peptide sequence has the sequence Ac-D$^-$-G-P-K$^+$-V-E$^-$//Nva-Y-N-K($\epsilon$-BFL)-NH$_2$ (SEQ ID NO:3). In some embodiments, the metalloprotease is MMP8 and the charge-changing peptide sequence has the sequence Ac-N-D$^-$-G-P-Q-G//Y-A-G-Q-G-A-G-diamino-ethyl-BFL (SEQ ID NO:4). In some embodiments, the metalloprotease is MMP9. In some embodiments, the cathepsin is selected from among cathepsin-S and cathepsin-D. In some embodiments, the cathepsin is cathepsin-S and the charge-changing peptide sequence has the sequence N-SUC$^-$-E$^-$G-R$^+$-W-H-T-V-G//L-R$^+$-W-E$^-$-C(Cy5$^-$)-R$^+$-CO-NH$_2$ (SEQ ID NO:5). In some embodiments, the cathepsin is cathepsin-D and the charge-changing peptide sequence has the sequence set forth in N-SUC$^-$-D$^-$-D$^-$-L-V-V-L//F-V-K$^+$K$^+$-C(Cy5$^-$)-A-CO-NH$_2$ (SEQ ID NO:6). In some embodiments, the bacterial protease is selected from among Omp-T and SspB. In some embodiments, the bacterial protease is Omp-T and the charge-changing peptide sequence has the sequence Ac-SUC$^-$-D$^-$-G-D$^-$-K$^+$-Y-R$^+$//R$^+$-A-W-G-D$^-$T-I-diamino-ethyl-BFL (SEQ ID NO:7). In some embodiments, the bacterial protease is SspB and the charge-changing peptide sequence has the sequence Ac-D$^-$-G-D$^-$-A-F-S//K$^+$-A-L-P-K($\epsilon$-BFL)-NH$_2$ (SEQ ID NO:8). In some embodiments, the kallikrein is selected from among kallikrein 2 and kallikrein 3. In some embodiments, the kallikrein is kallikrein 2 and the charge-changing peptide sequence has the sequence Ac-N-D$^-$-G-D$^-$-T-F-R$^+$//S-A-A-G-K($\epsilon$-BFL)-NH$_2$ (SEQ ID NO:9). In some embodiments, the kallikrein is kallikrein 3 and the charge-changing peptide sequence has the sequence Ac-N-D$^-$-G-S-S-I-Y//Q-S-S-T-G-diamino-ethyl-BFL (SEQ ID NO:10). In some embodiments, the calpain is selected from among calpain 1 and calpain 2. In some embodiments, the calpain is calpain 1 or calpain 2 and the charge-changing peptide sequence has the sequence N-SUC$^-$-E$^-$-P-L-F//A-A-R$^+$K($\epsilon$-BFL)-NH$_2$ (SEQ ID NO:11).

Detection of Amphiphilic Enzyme Substrates

Contact Angle Measurement

Figure 5A:
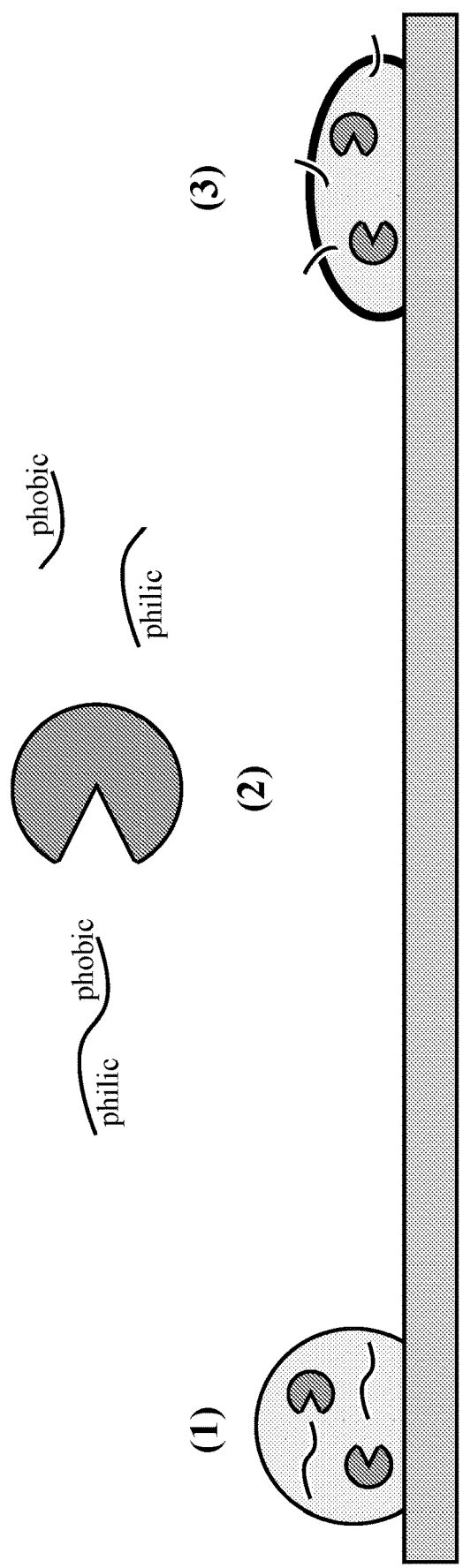

Provided herein are methods of detecting amphiphilic enzyme substrates. In some embodiments, the method includes measuring the contact angle of a sample droplet. In some embodiments, provided is a technique to detect protease activity in droplets of complex samples. In some embodiments, the complex biological sample is selected from among blood, plasma, and serum. In some embodiments, protease activity is detected by contact angle measurement (FIG. 5A). In some embodiments, the contact angle of a sample droplet indicates protease activity. In some embodiments, the protease activity yields hydrophobic products. In some embodiments, amphiphilic substrates are designed to contain a hydrophobic and hydrophilic section around a cleavage site for a protease of interest. In some embodiments, the substrates are incubated with a droplet of the complex sample. In some embodiments, the complex biological sample is selected from among blood, plasma, and serum. In some embodiments, proteolytic cleavage occurs. In some embodiments, proteolytic cleavage produces hydrophilic and hydrophobic products. In some embodiments, hydrophilic and hydrophobic products are released from the amphiphilic substrate as proteolytic cleavage occurs. In some embodiments, the hydrophobic cleavage products preferentially assemble at the droplet-air interface at the surface of the sample droplet. In some embodiments, the contact angle of the droplet decreases as more hydrophobic cleavage products migrate to the surface of the droplet. In some embodiments, the contact angle is measured as an indicator of protease activity.

Detection on Droplet Surface

Provided herein are methods of detecting amphiphilic enzyme substrates. In some embodiments, the method includes measuring fluorescence of a sample droplet. In some embodiments, provided is a technique to detect protease activity in droplets of complex samples. In some embodiments, the complex biological sample is selected from among blood, plasma, and serum. In some embodiments, protease activity is detected by fluorescence detection at the surface of the droplet (FIG. 5B). In some embodiments, fluorescently labeled amphiphilic substrates are designed to contain a hydrophobic and hydrophilic section around a cleavage site for a protease of interest. In some embodiments, the substrates are incubated with a droplet of a complex sample. In some embodiments, the complex biological sample is selected from among blood, plasma, and serum. In some embodiments, proteolytic cleavage occurs. In some embodiments, proteolytic cleavage produces hydrophilic and hydrophobic products. In some embodiments, hydrophilic and hydrophobic products are released from the amphiphilic substrate as proteolytic cleavage occurs. In some embodiments, the fluorescently labeled hydrophobic cleavage products preferentially assemble at the droplet-air interface at the surface of the sample droplet. In some embodiments, the fluorescence at the surface of the droplet is detected. In some embodiment, fluorescence at the surface of the droplet is an indicator of protease activity with minimal quenching by the sample.

Lateral Flow Assay Formats for Protease Detection Assays

Figure 6:
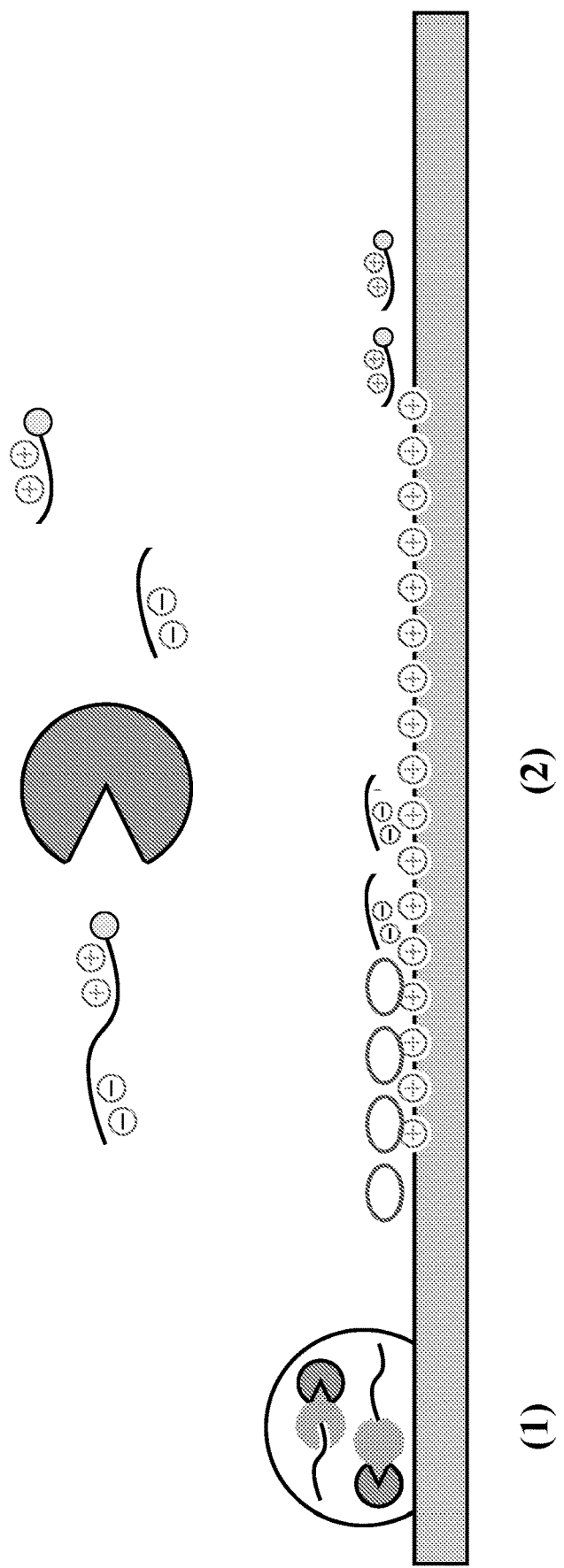
FIG. 6 is a lateral flow assay/thin layer chromatography of charge-changing substrate, showing (1) a neutral surface for sample incubation with the substrate and (2) a cationic surface that binds negative components of blood and causes positive cleavage product to associate with the liquid phase more than the solid phase.
Figure 8B:
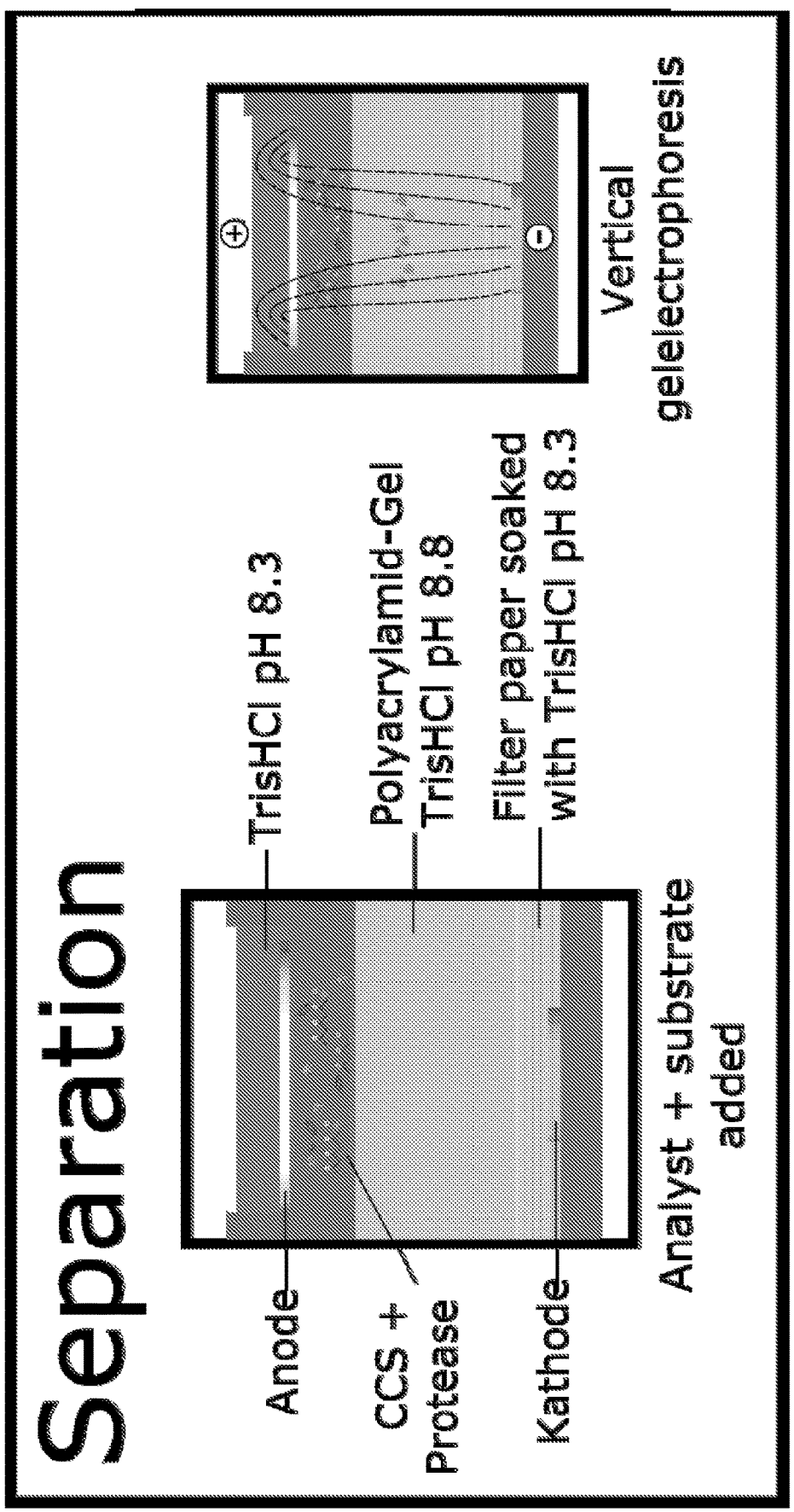

Provided herein is a lateral flow assay format for protease detection assays based on charge-changing substrates (FIG. 6). In some embodiments, neutral or negatively charged substrates are incubated with a complex sample on a neutral section of a lateral flow surface. In some embodiments, the complex biological sample is selected from among blood, plasma, and serum. In some embodiment, the neutral incubation section is adjacent to a cationic section of the lateral flow surface. In some embodiments, the sample components and negatively charged cleavage products associate with the positively charged solid surface. In some embodiments, the positively charged cleavage products are fluorescently or colorimetrically labeled. In some embodiments, the fluorescently or colorimetrically labeled, positively charged cleavage product associates with the liquid phase of the lateral flow assay. In some embodiments, the cationic surface binds the negative components of blood. In some embodiments, the cationic surface binds negative components of blood and causes positive cleavage products to associate with the liquid phase more than the solid phase. In some embodiments, the cleavage product migrates further than the sample components. In some embodiments, the cleavage product migrates further than the negatively charged cleavage products. In some embodiments, the cleavage product migrates further than the sample components and the negatively charged cleavage products. In some embodiments, the migrating positively charged cleavage products are detected by their fluorescent label. In some embodiments, the migrating positively charged cleavage products are detected by their colorimetric label. In some embodiments, the fluorescent or colorimentric label is detected as a band away from the quenching sample. In some embodiments, the band indicates protease activity.

Detection of Non-Degradative, Charge-Transferring Enzymes

Provided herein is a method of detecting non-degradative, charge-transferring enzymes in an unprocessed sample. In some embodiments, the method uses charge-changing substrates and electrophoretic separation from an unprocessed sample. In some embodiments, the non-degradative enzymes are selected from phosphorylases and kinases. In some embodiments, substrates with phosphorylated residues are incubated with complex samples (FIG. 7A). In some embodiments, the complex biological sample is selected from among blood, plasma, and serum. In some embodiments, the substrates with phosphorylated residues are selected from among serine, threonine, and tyrosine. In some embodiments, the substrates with phosphorylated residues are designed to become positively charged upon cleavage of the phosphate group. In some embodiments, cleavage of the phosphate group occurs by phosphorylases present in the sample. In some embodiments, the positively charged reaction product is separated from the complex sample. In some embodiments, the positively charged reaction product is separated from the complex sample by applying an electric field.

In some embodiments, positively charged substrates were incubated with complex samples. In some embodiments, the complex biological sample is selected from among blood, plasma, and serum. In some embodiments, the positively charged substrates contain residues selected from among serine, threonine, and tyrosine. In some embodiments, the substrates are designed to become negatively charged upon phosphorylation by kinases in the sample. In some embodiments, relative kinase activity across samples can be compared upon electrophoretic separation of phosphorylation products from the complex sample (FIG. 7B). In some embodiments, kinases add a negatively charged phosphate group to a substrate. In some embodiments, greater kinase activity results in reduced fluorescence compared to samples with less kinase activity as phosphorylated substrates become negatively charged and separate in the direction of the complex sample rather than the positively charged non-phosphorylated substrate. In some embodiments, kinase activity is inferred by measuring the reduction in fluorescence at the band of non-phosphorylated substrate in an electrophoresis gel.

AC/DC Electrokinetic Microarray Devices for Protease Detection Assays in Blood

The ability to carry out the detection of proteases and other disease-related enzymes using AC/DC electrokinetic microarray devices would have special advantages for developing highly sensitive and specific assays in point of care (POC) and other formats. However, a general problem for electronic microarray devices is the relatively low levels of AC and DC voltages and currents that can be applied to devices reduces their effectiveness in high conductance (>0.1 S/m) buffers and biological samples (blood, plasma, serum).

AC/DC Electrokinetic Microarray Devices

In one embodiment, provided herein are robust microarray devices that can be operated in both AC and DC modes. In some embodiments, each microelectrode is independently addressable by either direct micro-wiring or imbedded CMOS or other semiconductor control elements. In some embodiments, such devices are fabricated by photolithographic and other techniques well known for producing microelectronic devices. In some embodiments, microarrays are fabricated on silicon, glass, ceramic or plastic base substrate materials. In some embodiments, the microarrays are further insulated using silicon dioxide and silicon nitrate materials. In some embodiments, microelectrode and larger electrode structures are fabricated from platinum, palladium, gold, carbon, combinations thereof, or other conductor materials resistant to electrochemical degradation. In some embodiments, such microelectrodes and electrodes are fabricated onto the support structure using sputtering, e-beam or other deposition techniques well known to the microelectronics arts. In some embodiments, a key requirement is that the microelectrode structures is robust and resistant to electrochemical degradation. In some embodiments, microelectrodes are thicker (100 nm to 10 microns) and deposited under conditions which reduce defects and allow the microelectrodes/electrodes to function as a true solid metal. In some embodiments, microelectrodes on the array device have a variety of shapes which include, but are not limited to, circular, oval, rings, squares, rectangular and elongate wire like structures. In some embodiments, microelectrodes on the array device have a variety of sizes from 10 nm to 900 microns. In some embodiments, electrode structures range in size from 1 mm to 10 cm. In some embodiments, the number of microelectrodes on the array ranges from two to twenty thousand with spacing that ranges from 100 nm to 1 mm. In some embodiments, the microelectrode array structure is over coated with porous structure or permeation layer. In some embodiments this allows the sample solution (electrolyte, cations and anions) to contact the metal electrode surface, but prevents the larger biomolecules from reaching the surface where they can be damaged by the electrolysis products ($H^+$, $OH^-$, $O_2$, $H_2$, free radicals, heat, bubbles, etc.). Such permeation layers could include but are not limited to hydrogels (agarose, polyacrylamide, etc.), glass, organic, polymer, nylon net-like or porous structures; as well as lawns of nanostructures which achieve the desired permeation layer properties. In some embodiments, permeation layers range in thickness from 10 nm to 500 microns. In some embodiments, the permeation layer is impregnated with covalent and non-covalent binding agents. In some embodiments, the binding agents allow attachment of other binding agents. Such binding agents include, but are not limited to, amines, thiol groups, carboxyl groups, biotin, streptavidin, antibodies, aptamers, oligonucleotides, etc. In some embodiments, the binding agents are in specific areas of the microarray (on specific microelectrodes). In some embodiments, different binding agents are located in different areas of the microarray. In some embodiments, electrokinetic microarrays (chips) are enclosed in a sample chamber structure with associated microfluidics that allow samples, wash buffers and reagents to be delivered in a controlled manner. In some embodiments, the sample chamber structure has a component that secures the microarray (chip), prevents contact with the electrolyte and provides outside electrical connection to the microarray for providing the AC and DC voltages and currents required to carry out AC dielectrophoresis (DEP) and AC electrophoresis processes. In some embodiments, the sample chamber structure also has a glass, silica or plastic window over the microarray (chip) which would allow visual monitoring as well as color and/or epifluorescent detection. In some embodiments, the microarray (chip) enclosed in fluid sample chamber is connected to an AC/DC power supply and function generator; associated fluidic components for delivering samples, wash buffers and reagents and for accepting eluted samples and fluidic waste; visual monitoring and epifluorescent microscope and associated computer for overall control, chip monitoring, detection and analysis. In some embodiments, all components constitute a complete Protease Assay Detection System.

Microarray Protease Assays Carried Out in AC Mode

In the case of operating even a robust microarray device in the AC mode for dielectrophoretic (DEP) separations in blood, effective working voltages are limited to <25 volts AC before aggressive electrochemistry begins to disrupts the process. Under these conditions (<25 volts AC) red and white cells are concentrated into the DEP high field regions (between the microelectrodes), nanoscale entities (20 nm-800 nm) are concentrated into DEP high field regions (on the microelectrodes), while the smaller biomolecules remain relatively unaffected by the DEP fields. After the separation, a fluid wash can be used to remove the cells and other low molecular weight plasma components from the microarray device, while the nanoscale entities remain concentrated in the DEP high field areas.

In some embodiments, a protease assay on a microarray device operated in the AC mode utilizes special nanoparticle entities along with the charge changing peptide substrates which have affinity for the charge changing peptide products. In some embodiments, as the peptide substrates are cleaved by the protease in the blood, the charge changing peptide products become bound to the special nanoparticle entities. In some embodiments, these nanoparticle entities include, but are not limited to, fluorescent and non-fluorescent nanoparticles in size ranges from 20 nm to 800 nm; polymer, lipid based, metallic, semiconductor, and ceramic nanoparticles; nanoparticles with negative or positive charges, nanoparticles modified with ligand binding agents for covalent and noncovalent binding, including antibodies, aptamers and lectins. In some embodiments, after the protease reaction is complete, the AC field is applied and the nanoparticles with the bound peptide products are concentrated into the DEP high field areas on the microelectrodes, while blood cells are concentrated into the low field areas. In some embodiments, a fluid wash is then applied. In some embodiments, the fluid wash removes the blood cells and plasma components along with any unreacted charge changing peptide substrate. In some embodiments, the nanoparticles-peptide products remain concentrated in the DEP high field area where they are detected.

In some embodiments, specific protease assays are carried out using negatively charged fluorescent charge changing peptide substrates that produce positively charged fluorescent peptide products together with negatively charged non-fluorescent nanoparticles. In some embodiments, upon cleavage by the specific protease in the blood, the positively charged fluorescent peptide product binds to the negatively charged non-fluorescent nanoparticles. In some embodiments, the AC field is applied and the nanoparticles with bound fluorescent charge changing peptide product are isolated into the DEP high field regions. In some embodiments, a fluidic wash is then used to remove the cells, plasma materials, and any un-reacted negatively charged fluorescent charge changing peptide substrate. In some embodiments, the nanoparticle-fluorescent peptide product remains isolated on the microelectrodes for epifluorescent detection and analysis. This example involving a negatively charged fluorescent charge changing peptide with negatively charged non-fluorescent nanoparticles is shown in FIG. 7. Many other such AC/DC microarray assay formats are within the scope of this invention, one further example would include using non-fluorescent nanoparticles labelled with antibodies which are specific for the charge changing peptide products. Many other AC mode assay formats are possible.

Microarray Protease Assays Carried Out in DC Mode

In the case of operating even a robust microarray device in the DC mode for electrophoretic based separations in blood, effective working voltages are limited to <10 volts DC before aggressive electrochemistry begins to disrupts the process. An additional problem for DC mode operations is that the electrophoretic attraction of charged entities like the peptide substrates and products is greatly reduced in high conductance (>0.5 S/m) buffers and biological samples (blood, plasma, serum).

In some embodiments, provided are novel methods and procedures that allow protease assays and detection of charge-changing peptide products to be carried out by microarray devices operated in the DC mode. By way of just one of many examples, a blood sample with a specific negatively charged fluorescent charge changing peptide substrate would be applied to the microarray chip device. After the appropriate reaction time, a DC field would be applied to the chip with a group of microelectrodes near to the fluidic input port biased negative and a group of microelectrodes near to the outlet port biased positive. At the same time, a wash solution containing a low conductance zwitterionic buffer would be slowly delivered to the chip through the inlet port. As the low conductance buffer moves over the chip the positively charged fluorescent charge changing peptide products will become more electrophoretically attracted to the negatively charged microelectrodes on one side of the chip device while all other components, cells, plasma proteins and negatively charged fluorescent charge changing peptide substrates are electrophoretically attracted to the opposite side of the microarray. Ultimately, the flow of the wash fluid will remove most of the cells and plasma proteins, while the positively charged fluorescent charge changing peptide products remain concentrated on the set of microelectrodes near the input port. At this point the fluorescent peptide products can be detected and analyzed by epifluorescence. In this procedure, low conductance buffers can include but are not limited to zwitterionic histidine buffer in the 1 mM to 100 mM range. Many other DC mode separation formats and detection schemes are well within the scope of this invention.

EXAMPLES

Example 1: Identifying the Proteolytic Signature of Complex Samples

A synthetic peptide library containing combinations of amino acid pairs, combinations of positively and negatively charged residues or modified residues at different positions along the length of the synthetic peptides, and a tag such as a fluorescent dye was prepared (FIG. 1A). Substrate signatures were generated after an incubation of complex samples (e.g., blood, plasma, serum) with the substrate library and separation of the cleavage products of the incubated substrate library from the complex sample by gel electrophoresis, capillary electrophoresis, or a combination of DC and AC electrokinetic techniques.

Individual substrates in the peptide mixture were ranked according to migration and detected via fluorescence or other tag. To dissect the contribution of multiple classes of protease activity such as serine, cysteine, and metallopeptidases, samples were tested after being incubated separately with various activity inhibitors such as the metal chelator EDTA, the cysteine peptidase inhibitors E-64 and CAO74, or the elastase-specific chloromethyl ketone inhibitor. Cleavage-site specificity data from inhibited samples was combined to generate a substrate signature for each peptidase class. Secondary synthetic peptide libraries were generated to further define the cleavage preferences of peptidases in complex samples.

Example 2: In Vitro/In Vivo Purification by Activity Based Probes

An ABP composed of a chemically reactive group attached to a positively charged moiety via a spacer molecule was designed (FIGS. 2A-2D). The ABP was incubated with a sample in vitro or injected in vivo. Upon binding of the ABP to the protease active site, the chemically reactive group reacted irreversibly with the active site nucleophilic residue. The positively charged moiety of the ABP remained exposed outside the active site of the protease. Electrophoretic separation in vitro was used to separate the proteases that have bound ABP since the positively charged moiety separated from the majority of components of the complex biological sample that were negatively charged. Following in vivo injection of an ABP with a positively charged moiety and an identifying tag such as a near-infrared or fluorescent dye, visualization of protease activity was possible, such as at the site of a tumor which was biopsied. After biopsy the ABP-bound proteases were separated from the complex sample by electrophoretic separation. ABP-bound proteases that had been separated from complex samples were available for further downstream applications and characterization of post-translational modifications, mutations, etc.

Example 3: In Vivo Protease Detection by Peptides

A negatively charged fluorescently labeled peptide was injected into a mouse. Upon encountering the acidic microenvironment of a tumor, the histidine residues of the peptide became positively charged and the peptide was overall neutral, which allowed the peptide to penetrate the tumor. The peptide was cleaved by the protease for which its sequence was designed. The positively charged, fluorescent or near-infrared labeled cleavage product stuck to the cell surface and allowed in vivo imaging of protease activity and localization (FIGS. 3A-3D).

Example 4: In Vivo Protease Detection by Peptide Decorated Nanoparticles

A nanoparticle decorated with negatively charged peptides was injected into a mouse. Upon encountering the acidic microenvironment of a tumor, the histidine residues of the peptide became positively charged and the peptide was overall neutral, which allowed the decorated nanoparticle to penetrate the tumor. The peptide on the surface of the nanoparticle was cleaved by the protease for which its sequence was designed. The cleavage product was positively charged which caused the decorated nanoparticle to stick to the cell surface and release its payload of imaging agents and/or drug molecules into the tumor cell (FIGS. 4A-4E).

Example 5: Detection of Amphiphilic Enzyme Substrates Using Contact Angle Measurement A technique to detect protease activity in droplets of complex samples by contact angle measurement was developed (FIG. 5A). Amphiphilic substrates were designed that contained a hydrophobic and hydrophilic section around a cleavage site for a protease of interest. The substrates were incubated with a droplet of a complex sample (e.g., blood) and as proteolytic cleavage occurred, hydrophilic and hydrophobic products were released from the amphiphilic substrate. The hydrophobic cleavage products preferentially assembled at the droplet-air interface at the surface of the sample droplet. As more hydrophobic cleavage products migrated to the surface of the droplet, the contact angle of the droplet decreased and was measured as an indicator of protease activity.

Example 6: Detection of Amphiphilic Enzyme Substrates on Droplet Surfaces

A technique to detect protease activity in droplets of complex samples by fluorescence detection at the surface of the droplet was developed (FIG. 5B).

Fluorescently labeled amphiphilic substrates were designed to contain a hydrophobic and hydrophilic section around a cleavage site for a protease of interest. The substrates were incubated with a droplet of a complex sample (e.g., blood), and as proteolytic cleavage occurred, hydrophilic and hydrophobic products were released from the amphiphilic substrate. The fluorescently labeled hydrophobic cleavage products preferentially assembled at the droplet-air interface at the surface of the sample droplet. The fluorescence at the surface of the droplet was detected as an indicator of protease activity with minimal quenching by the sample.

Example 7: Lateral Flow Assays of Charge-Changing Substrates

A lateral flow assay format for protease detection assays based on charge-changing substrates was developed (FIG. 6). Neutral or negatively charged substrates were incubated with complex sample on a neutral section of a lateral flow surface. The neutral incubation section was adjacent to a cationic section of the lateral flow surface that caused sample components and negatively charged cleavage products to associate with the positively charged solid surface. The fluorescently or colorimetrically labeled positively charged cleavage product associated with the liquid phase of the lateral flow assay and migrated further than the sample components or the negatively charged cleavage products. The migrating positively charged cleavage products were detected by their fluorescent or colorimetric label as a band away from the quenching sample which indicated protease activity.

Example 8: Detection of Non-Degradative, Charge-Transferring Enzymes

A method by which to measure non-degradative, charge-transferring enzymes such as kinases and phosphorylases based on charge-changing substrates and electrophoretic separation from complex samples was developed. Substrates with phosphorylated residues such as serine, threonine, and tyrosine, were incubated with complex samples and were designed to become positively charged upon cleavage of the phosphate group by phosphorylases present in the sample (FIG. 7A). The positively charged reaction product was then separated from the complex sample by applying an electric field.

Positively charged substrates containing residues such as serine, threonine, and tyrosine, were incubated with complex samples and were designed to become negatively charged upon phosphorylation by kinases in the sample (FIG. 7B). Relative kinase activity across samples was compared upon electrophoretic separation of phosphorylation products from the complex sample. Greater kinase activity resulted in reduced fluorescence compared to samples with less kinase activity as phosphorylated substrates became negatively charged and separated in the direction of the complex sample rather than the positively charged non-phosphorylated substrate. Kinase activity was inferred by measuring the reduction in fluorescence at the band of non-phosphorylated substrate in an electrophoresis gel.

Example 9: Thrombin Detection Using a Charge-Changing Peptide

Figure 10B:
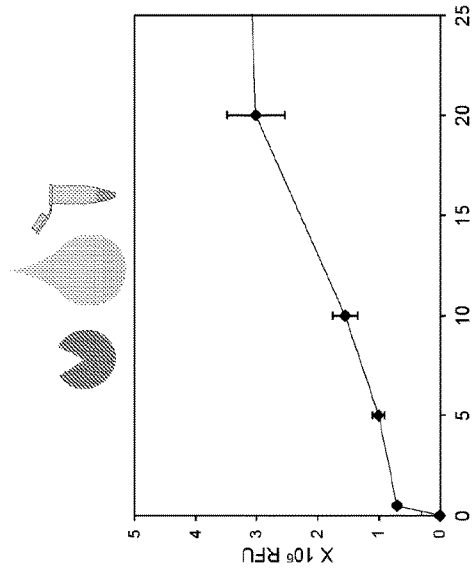
FIGS. 10A-10D show thrombin detection using a thrombin-specific charge-changing peptide substrate.
Figure 10D:
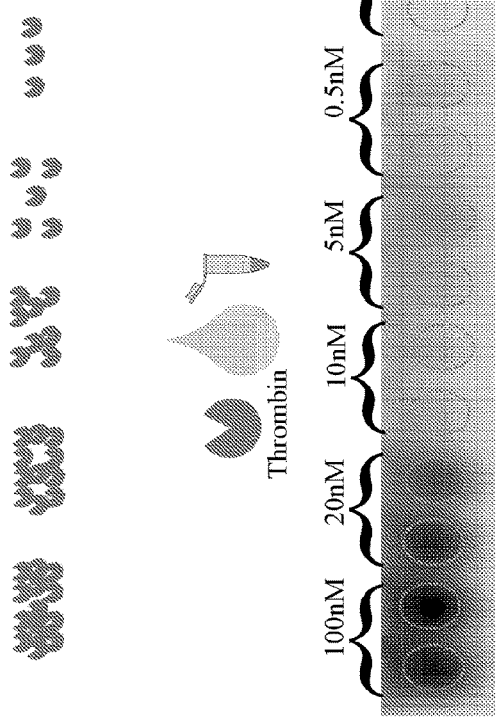
Figure 10A:
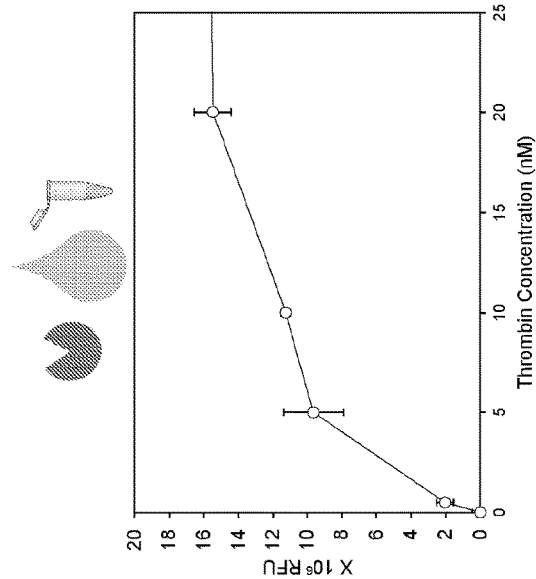
Figure 10C:
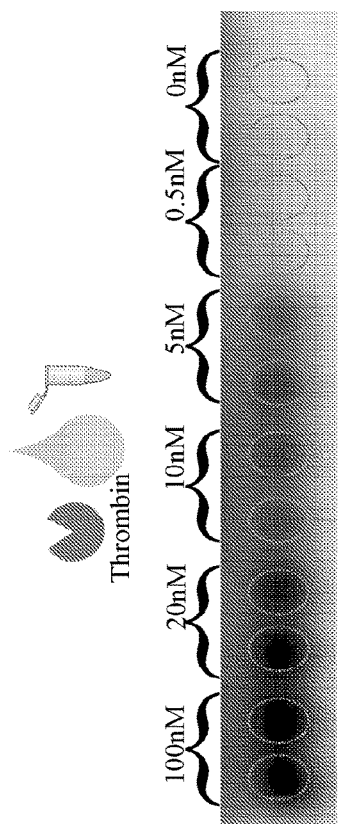

Various concentrations (0 nM, 0.5 nM, 5 nM, 10 nM, 20 nM, or 100 nM) of the thrombin targeted charge-changing peptide shown in FIG. 9 (and with the sequence Ac-N-D$^-$-D$^-$-Nle-T-P-R$^+$//G-S-A-G-A-G-A-G-diamino-ethyl-BFL (SEQ ID NO:1)) was incubated in either 1×PBS (FIG. 10A) or citrated blood (FIG. 10B), both of which contained thrombin. After incubation, fluorescence was measured, indicating specific binding of the peptide to the thrombin in the sample. Fluorescence increased with increasing thrombin concentration.

Example 10: Whole Blood Thrombin Detection

The thrombin targeted charge-changing peptide shown in FIG. 9 (and with the sequence Ac-N-D$^-$-D$^-$-Nle-T-P-R$^+$//G-

S-A-G-A-G-A-G-diamino-ethyl-BFL (SEQ ID NO:1)) was incubated in untreated whole blood for up to 33 minutes. A negative control was also prepared See FIG. 11A. Fluorescence was measured at 3 minute intervals during incubation. Fluorescence signal, indicating specific binding of the peptide to thrombin in the whole blood sample, increased over time, with peak values observed after about 18 minutes (FIG. 11B).

Example 11: Cathepsin-S Detection in Buffer

The cathepsin-S targeted charge-changing peptide shown in FIG. 9 (and with the sequence N-SUC$^-$-E$^-$-G-R$^+$-W-H-T-V-G//L-R$^+$-W-E$^-$-C(Cy5$^-$)-R$^+$CO-NH$_2$ (SEQ ID NO:5)) was incubated in 1×PBS buffer with varying concentrations of cathepsin-S. After incubation, fluorescence was measured, indicating specific binding of the peptide to the cathepsin-S in the sample. Fluorescence increased with increasing cathepsin-S concentration (FIG. 12).

Example 12: Coagulation Monitoring

Figure 13B:
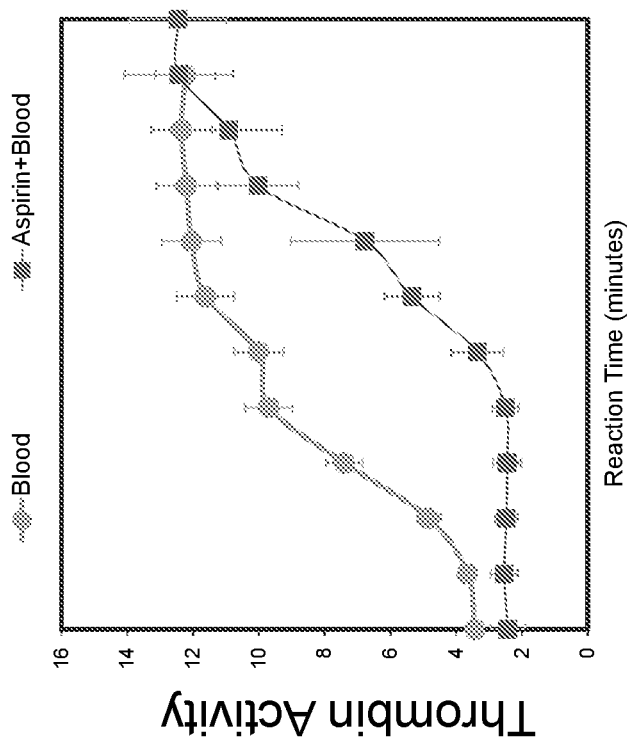
FIGS. 13A-13B illustrate thrombin activity in blood samples from subjects taking an anticoagulant (aspirin) vs. control.
Figure 13A:
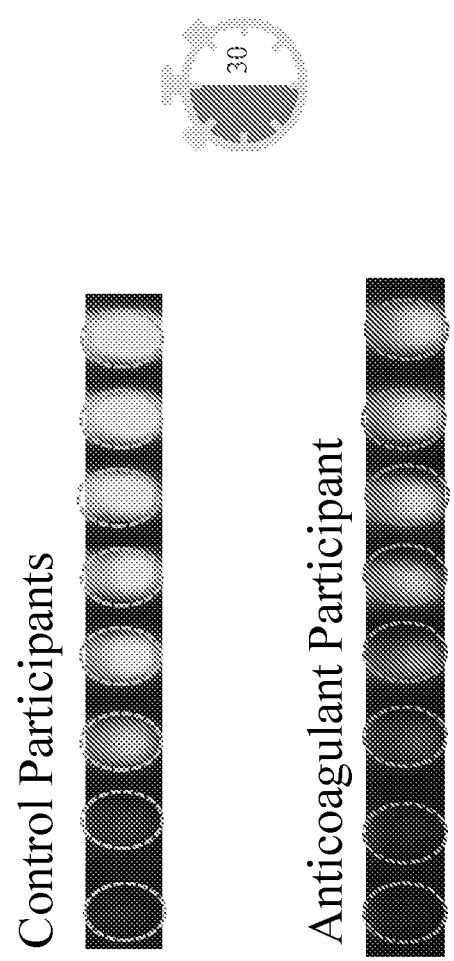
Figure 14A:
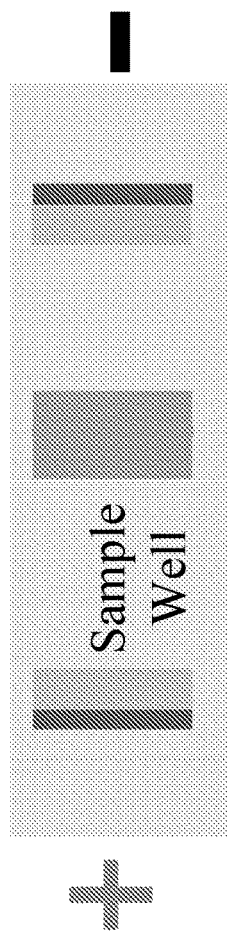
FIGS. 14A-14C illustrate a prototype for coagulation monitoring in real time. A sample is placed in a sample well with a peptide substrate (e.g., a charge-changing peptide substrate) (FIG. 14A), fluorescence is measured at to (FIG. 14B, top panel) and again at a later time points (FIG. 14B, bottom panel).
Figure 14C:
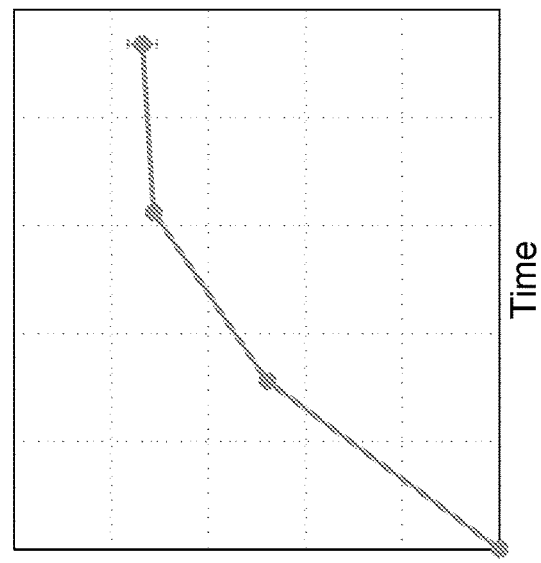
Figure 14B:
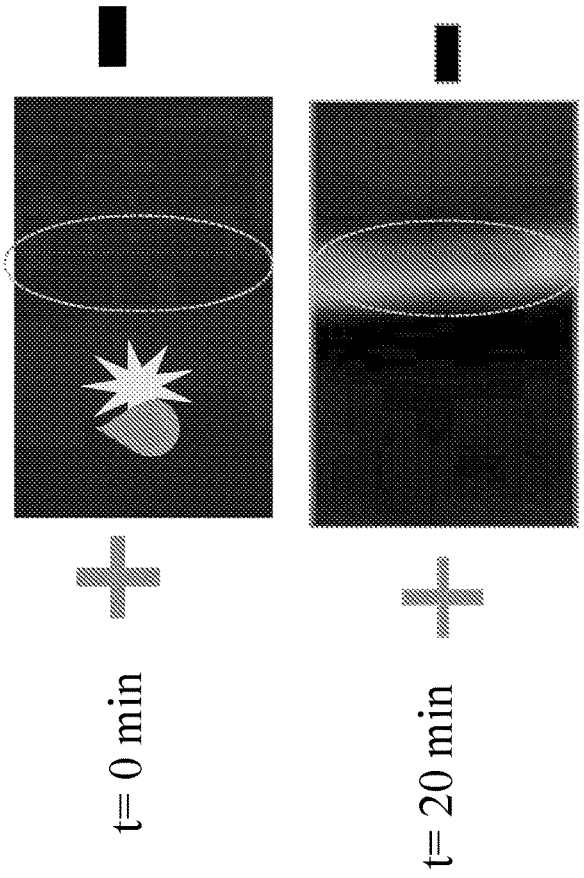

To detect thrombin activity and monitor coagulation, the thrombin targeted charge-changing peptide shown in FIG. 9 (and with the sequence of Ac-N-D$^-$-D$^-$-Nle-T-P-R$^+$//G-S-A-G-A-G-A-G-diamino-ethyl-BFL (SEQ ID NO:1)) was incubated in a drop of whole blood from subjects taking an anticoagulant (aspirin) and from control subjects that were not taking an anticoagulant. Fluorescence signal, indicating specific binding of the peptide to thrombin in the whole blood sample, was measured at various time points up to 30 minutes. The top panel of FIG. 13A shows fluorescence in the control group while the bottom panel shows fluorescence in the anticoagulant group. Fluorescence increased in both subject groups over time, but more quickly in the control group (FIG. 13B).

Figure 15B:
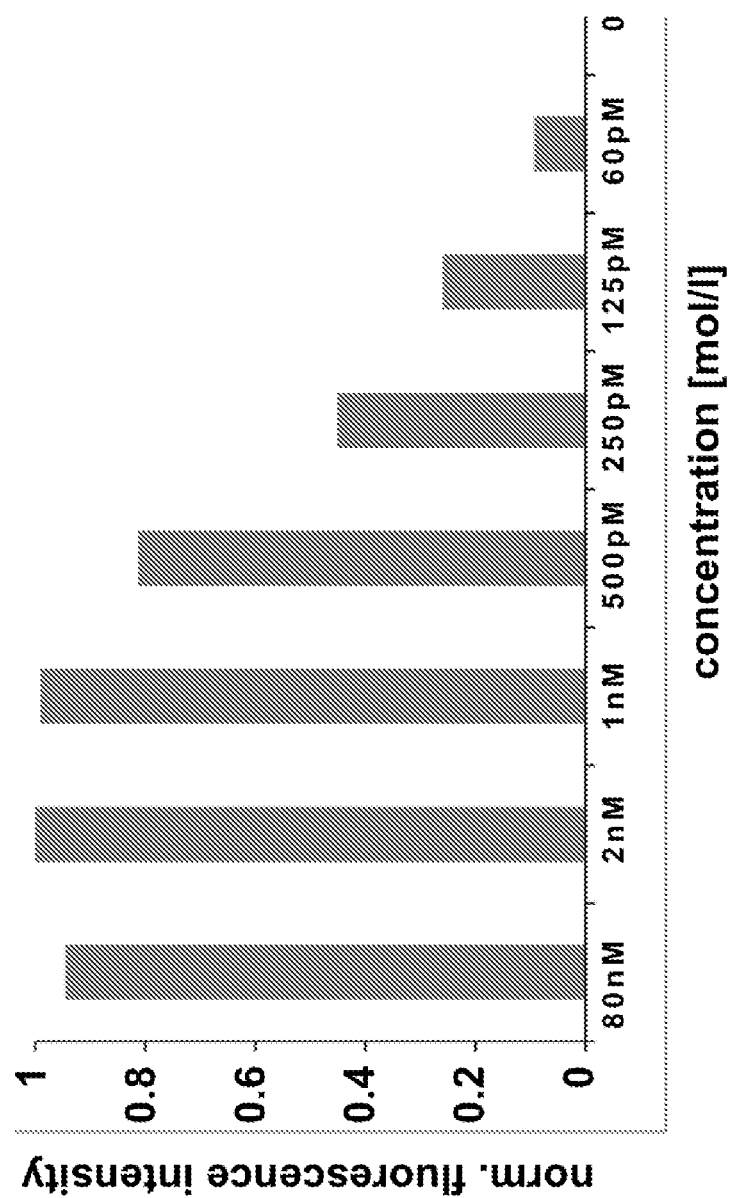
FIGS. 15A-15B show a miniaturized array prototype.
Figure 15A:
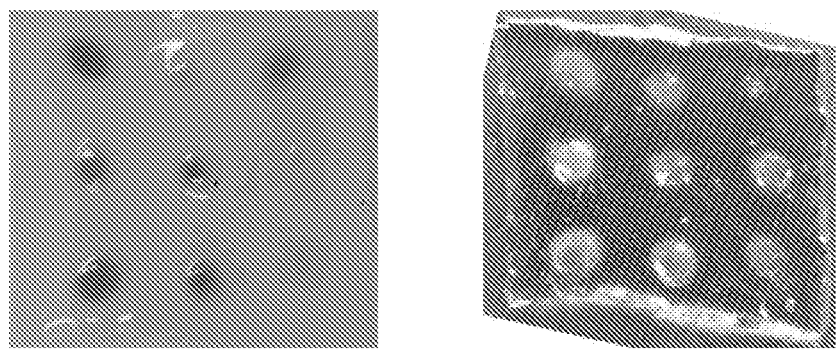

Example 13: Protease (Trypsin) Activity Measurements Using an Electrophoresis Focusing Assay and Miniaturized Array Prototype A miniaturized array prototype was used to measure trypsin activity using an electrophoresis focusing assay (FIG. 15A). A charge-changing trypsin-specific peptide with a fluorescent tag was incubated with sample containing various concentrations of trypsin. Electrophoretic separation was used to separate trypsin bond to a charge-changing peptide substrate. The trypsin with bound substrate were positively charged and separated from the majority of components of the complex biological sample that were negatively charged. Increased fluorescence was observed with an increase in concentration of trypsin (FIG. 15B).

Figure 16B:
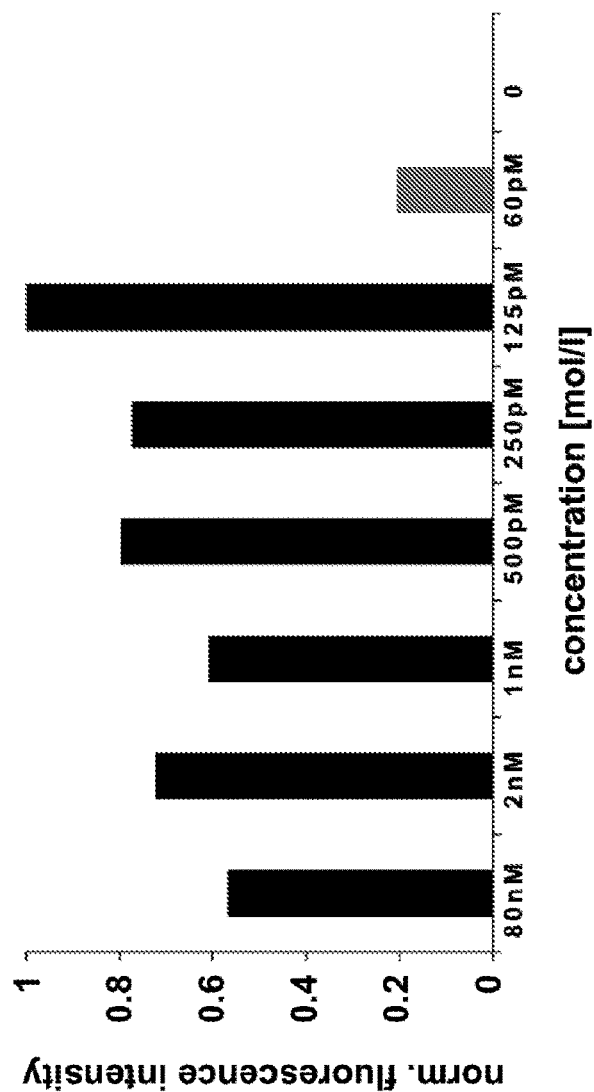
FIGS. 16A-16B show a miniaturized array prototype.
Figure 16A:
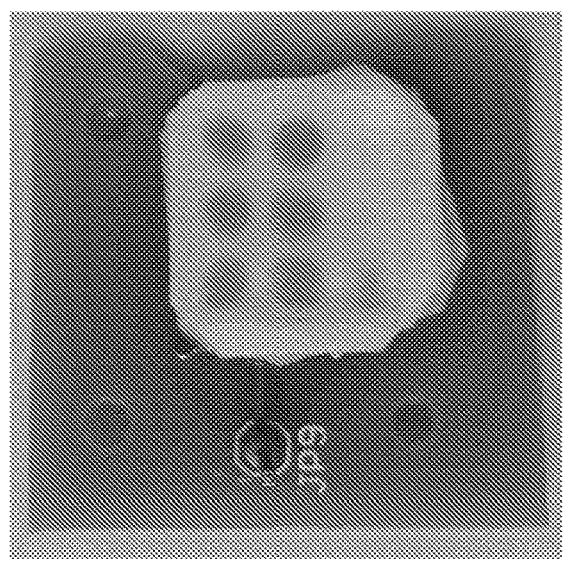

Trypsin activity was measured after one week using a miniaturized array prototype (FIG. 16A). Increased fluorescence was observed with an increase in concentration of trypsin (FIG. 16B).

Figure 17B:
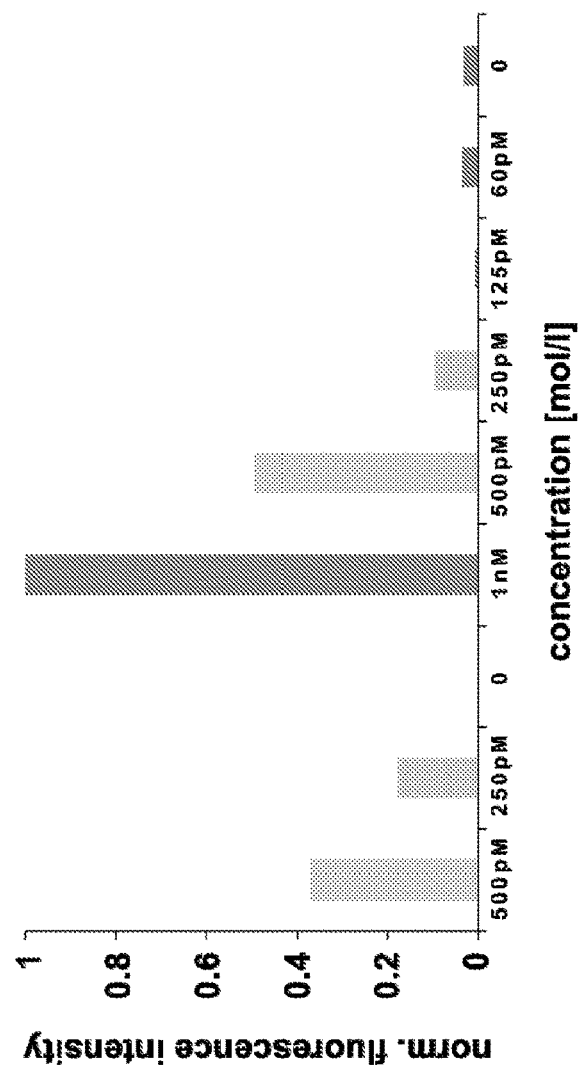
FIGS. 17A-17B show a miniaturized array prototype.
Figure 17A:
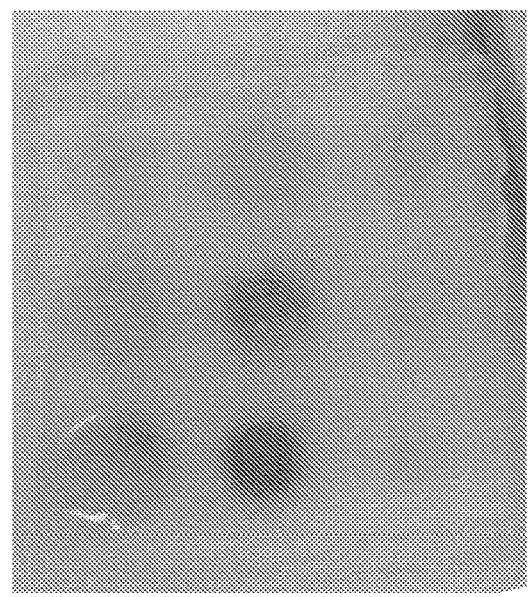
Figure 18A:
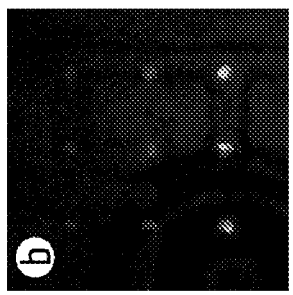
FIGS. 18A-D show a miniaturized array prototype and results of an electrophoresis focusing assay.
Figure 18B:
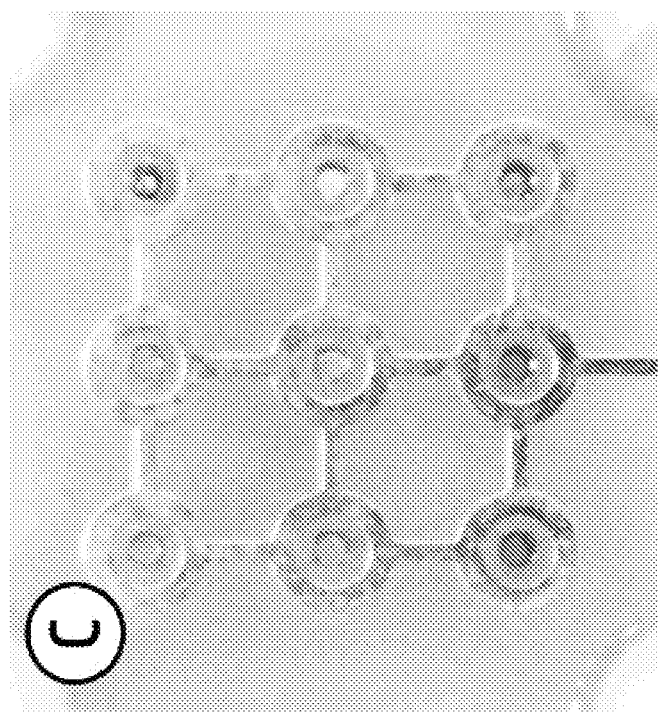
Figure 18C:
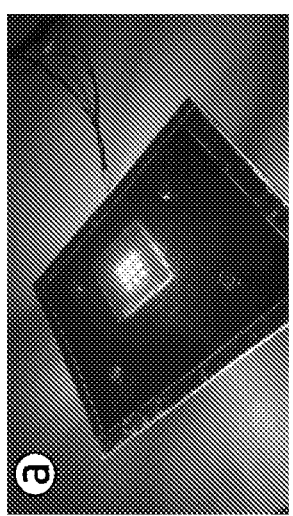
Figure 18D:
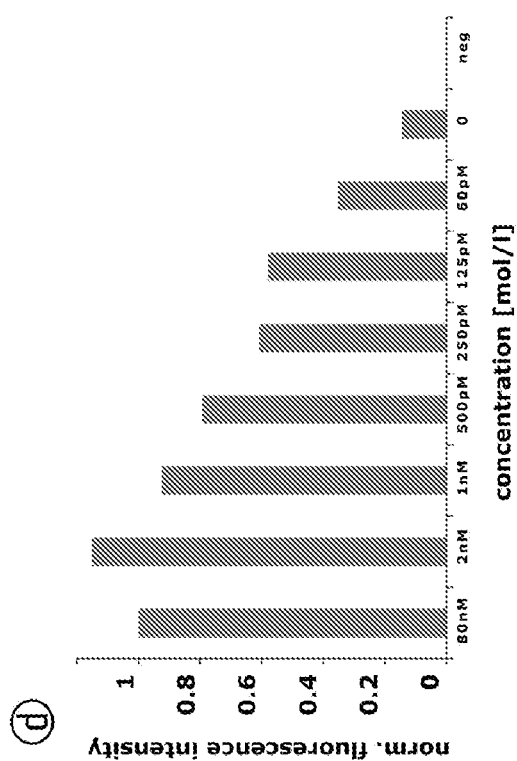

Trypsin activity was also measured in a blood sample using a miniaturized array prototype (FIG. 17A). Increased fluorescence was observed with an increase in concentration of trypsin (FIG. 17B).

Example 14: Concentration and Detection of Proteases Using DEP

Figure 19:
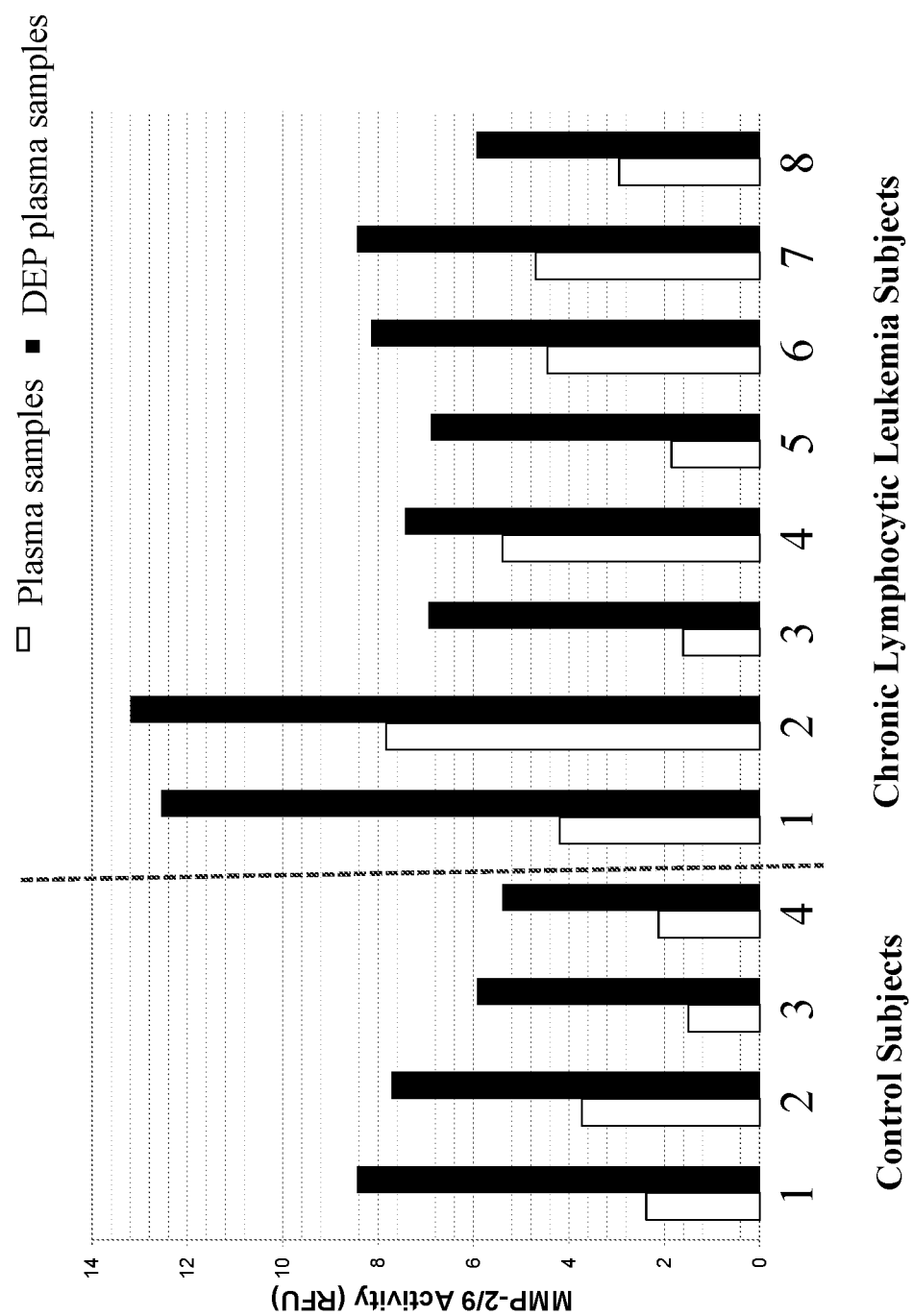
FIG. 19 shows detection of MMP2 and MMP activity in plasma samples from chronic lymphocytic leukemia subjects vs. control in plasma samples (white bars) and plasma samples subjected to dielectrophoretic (DEP) separation (black bars).

Dielectrophoretic (DEP) separation was used to detect and determine concentration of MMP2 and MMP9 in plasma samples from chronic lymphocytic leukemia subjects and compared to control subjects. Plasma samples were incubated with a charge-changing peptide substrate specific for MMP2/9. An AC field was applied to some of the plasma samples and the proteases with bound fluorescent charge changing peptide product were isolated into the DEP high field regions. As shown in FIG. 19, fluorescence intensity was greater in all subjects in the DEP plasma samples (black bars) as compared to plasma samples not subjected to DEP (white bars).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Biological significance of proteolytic and post-translational modifications Barrett, A. J. (2004) Bioinformatics of proteases in the MEROPS database. *Curr. Opin. Drug. Discov. Dev.* 7, 334-341.
Cohen, P. (2002) The origins of protein phosphorylation. *Nat. Cell Biol.* 4, E127-E130.
Daviet, L., and Colland, F. (2008) Targeting ubiquitin specific proteases for drug discovery. *Biochimie (Paris)* 90, 270-283.
Geiss-Friedlander, R., and Melchior, F. (2007) Concepts in sumoylation: a decade on. *Nat. Rev. Mol. Cell Biol.* 8, 947-956.
Nandi, D., Tahiliani, P., Kumar, A., and Chandu, D. (2006) The ubiquitin-proteasome system. *J. Biosci.* 31, 137-155.
Polevoda, B., and Sherman, F. (2003) N-terminal acetyltransferases and sequence requirements for N-terminal acetylation of eukaryotic proteins. *J. Mol. Biol.* 325, 595-622.
Puente, X. S., Sanchez, L. M., Overall, C. M., and López-Otín, C. (2003) Human and mouse proteases: a comparative genomic approach. *Nat. Rev. Genet.* 4, 544-558.
Sadoul, K., Boyault, C., Pabion, M., and Khochbin, S. (2008) Regulation of protein turnover by acetyltransferases and deacetylases. *Biochimie (Paris)* 90, 306-312.
Walsh, G., and Jefferis, R. (2006) Post-translational modifications in the context of therapeutic proteins. *Nat. Biotechnol.* 24, 1241-1252.
Diseases and Therapy Targeting of Proteases and Post-Translational Enzymes
Coussens, L. M., Fingleton, B., Matrisian, L. M. (2002) Matrix metalloproteinase inhibitors and cancer: trials and tribulations. *Science* 295, 2387-2392.
Drag, M., and Salvesen, G. S. (2010) Emerging principles in protease-based drug discovery. *Nat. Rev. Drug Discovery* 9, 690-701.
Gutierrez-Fernandez, A., Fueyo, A., Folgueras, A. R., Garabaya, C., Pennington, C. J., Pilgrim, S., Edwards, D. R., Holliday, D. L., Jones, J. L., Span, P. N., Sweep, F. C., Puente, X. S., and López-Otín, C. (2008) Matrix metalloproteinase-8 functions as a metastasis suppressor through modulation of tumor cell adhesion and invasion. *Cancer Res.* 68, 2755-2763.
Hegedus, L., Cho, H., Xie, X., and Eliceiri, G. L. (2008) Additional MDA-MB-231 breast cancer cell matrix metalloproteinases promote invasiveness. *J. Cell. Physiol.* 216, 480-485.

McQuibban, G. A., Gong, J. H., Tam, E. M., McCulloch, C. A., Clark-Lewis, I., and Overall, C. M. (2000) Inflammation dampened by gelatinase A cleavage of monocyte chemoattractant protein-3. *Science* 289, 1202-1206.

McQuibban, G. A., Gong, J. H., Wong, J. P., Wallace, J. L., Clark-Lewis, I., and Overall, C. M. (2002) Matrix metalloproteinase processing of monocyte chemoattractant proteins generates CC chemokine receptor antagonists with anti-inflammatory properties in vivo. *Blood* 100, 1160-1167.

Overall, C. M., and Kleifeld, O. (2006) Towards third generation matrix metalloproteinase inhibitors for cancer therapy. *Br. J. Cancer* 94, 941-946.

Overall, C. M., and Kleifeld, O. (2006) Tumour microenvironment—opinion: validating matrix metalloproteinases as drug targets and anti-targets for cancer therapy. *Nat. Rev. Cancer* 6, 227-239.

Stoch, S. A., and Wagner, J. A. (2008) Cathepsin K inhibitors: a novel target for osteoporosis therapy. *Clin. Pharmacol. Ther.* 83, 172-176.

Tremblay, G. M., Janelle, M. F., and Bourbonnais, Y. (2003) Anti-inflammatory activity of neutrophil elastase inhibitors. *Curr. Opin. Investig. Drugs* 4, 556-565.

Turk, B. (2006) Targeting proteases: successes, failures and future prospects. *Nat. Rev. Drug Discov.* 5, 785-799.

Yang, X., Dong, Y., Zhao, J., Sun, H., Deng, Y., Fan, J., and Yan, Q. (2007) Increased expression of human macrophage metalloelastase (MMP-12) is associated with the invasion of endometrial adenocarcinoma. *Pathol. Res. Pract.* 203, 499-505.

Microarray Technologies for Degradomics

Chen, G. Y., Uttamchandani, M., Zhu, Q., Wang, G., Yao, S. Q. (2003) Developing a strategy for activity-based detection of enzymes in a protein microarray. *ChemBioChem* 4, 336-339.

Eppinger, J., Funeriu, D. P., Miyake, M., Denizot, L., Miyake, J. (2004) Enzyme Microarrays: On-Chip Determination of Inhibition Constants Based on Affinity-Label Detection of Enzymatic Activity. *Angew. Chem.* 116, 3894-3898.

Funeriu, D. P., Eppinger, J., Denizot, L., Miyake, M., Miyake, J. (2005) Enzyme family-specific and activity-based screening of chemical libraries using enzyme microarrays. *Nat. Biotechnol.* 23, 622-627.

Overall, C. M., Tam, E. M., Kappelhoff, R., Connor, A., Ewart, T., Morrison, C. J., Puente, X., López-Otín, C., and Seth, A. (2004) Protease degradomics: mass spectrometry discovery of protease substrates and the CLIP-CHIP, a dedicated DNA microarray of all human proteases and inhibitors. *Biol. Chem.* 385, 493-504.

Pease, A. C., Solas, D., Sullivan, E. J., Cronin, M. T., Holmes, C. P., Fodor, S. P. (1994) Light-generated oligonucleotide arrays for rapid DNA sequence analysis. *Proc. Natl. Acad. Sci. USA* 91, 5022-5026.

Sieber, S. A., Mondala, T. S., Head, S. R., Cravatt, B. F. (2004) Microarray platform for profiling enzyme activities in complex proteomes. *J. Am. Chem. Soc.* 126, 15640-15641.

Uttamchandani, M., Liu, K., Panicker, R. C., Yao, S. Q. (2007) Activity-based fingerprinting and inhibitor discovery of cysteine proteases in a microarray. *Chem. Commun.* 1518-1520.

Winssinger, N., Damoiseaux, R., Tully, D. C., Geierstanger, B. H., Burdick, K., Harris, J. L. (2004) PNA-encoded protease substrate microarrays. *Chem. Biol.* 11, 1351-1360.

Wu, H., Ge, J., Yang, P.-Y., Wang, J., Uttamchandani, M., Yao, S. Q. (2011) A peptide aldehyde microarray for high-throughput profiling of cellular events. *J. Am. Chem. Soc.* 133, 1946-1954.

Mass Spectrometry Technologies for Degradomics

Aebersold, R., and Mann, M. (2003) Mass spectrometry-based proteomics. *Nature* 422, 198-207.

Dean, R. A. and Overall, C. M. (2007) Proteomics discovery of metalloproteinase substrates in the cellular context by iTRAQ labeling reveals a diverse MMP-2 substrate degradome. *Mol. Cell Proteomics* 6, 611-623.

Domon, B., and Aebersold, R. (2006) Mass spectrometry and protein analysis. *Science* 312, 212-217.

López-Otín, C., and Overall, C. M. (2002) Protease degradomics: a new challenge for proteomics. *Nat. Rev. Mol. Cell Biol.* 3, 509-519.

Mann, M., Hendrickson, R. C., and Pandey, A. (2001) Analysis of proteins and proteomes by mass spectrometry. *Annu. Rev. Biochem.* 70, 437-473.

O'Donoghue, A. J., Eroy-Reveles, A. A., Knudsen, G. M., Ingram, J., Zhou, M., Statnekov, J. B., . . . Craik, C. S. (2012) Global identification of peptidase specificity by multiplex substrate profiling. *Nature Methods,* 9(11), 1095-1100.

Overall, C. M., Tam, E. M., Kappelhoff, R., Connor, A., Ewart, T., Morrison, C. J., Puente, X., López-Otín, C., and Seth, A. (2004) Protease degradomics: mass spectrometry discovery of protease substrates and the CLIP-CHIP, a dedicated DNA microarray of all human proteases and inhibitors. *Biol. Chem.* 385, 493-504.

Schwartz, D. R., Moin, K., Yao, B., Matrisian, L. M., Coussens, L. M., Bugge, T. H., Fingleton, B., Acuff, H. B., Sinnamon, M., Nassar, H., Platts, A. E., Krawetz, S. A., Linebaugh, B. E., and Sloane, B. F. (2007) Hu/Mu ProtIn oligonucleotide microarray: dual-species array for profiling protease and protease inhibitor gene expression in tumors and their microenvironment. *Mol. Cancer Res.* 5, 443-54.

Activity-Based Probes and Mass Spectrometry Analysis for Degradomics

Blum, G., von Degenfeld, G., Merchant, M. J., Blau, H. M., and Bogyo, M. (2007) Noninvasive optical imaging of cysteine protease activity using fluorescently quenched activity-based probes. *Nat. Chem. Biol.* 3, 668-677

Chan, E. W., Chattopadhaya, S., Panicker, R. C., Huang, X., and Yao, S. Q. (2004) Developing photoactive affinity probes for proteomic profiling: hydroxamate-based probes for metalloproteases. *J. Am. Chem. Soc.* 126, 14435-14446.

Chun, J., Yin, Y. I., Yang, G., Tarassishin, L., and Li, Y. M. (2004) Stereoselective synthesis of photoreactive peptidomimetic γ-secretase inhibitors. *J. Org. Chem.* 69, 7344-7347.

Grabarek, J., and Darzynkiewicz, Z. (2002) In situ activation of caspases and serine proteases during apoptosis detected by affinity labeling their enzyme active centers with fluorochrome-tagged inhibitors. *Exp. Hematol.* 30, 982-989.

Greenbaum, D., Medzihradszky, K. F., Burlingame, A., and Bogyo, M. (2000) Epoxide electrophiles as activity-dependent cysteine protease profiling and discovery tools. *Chem. Biol.* 7, 569-581.

Greenbaum, D., Baruch, A., Hayrapetian, L., Darula, Z., Burlingame, A., Medzihradszky, K. F., and Bogyo, M. (2002) Chemical approaches for functionally probing the proteome. *Mol. Cell. Proteomics* 1, 60-68.

Kessler, B. M., Tortorella, D., Altun, M., Kisselev, A. F., Fiebiger, E., Hekking, B. G., Ploegh, H. L., and Overkleeft, H. S. (2001) Extended peptide-based inhibitors efficiently target the proteasome and reveal overlapping specificities of the catalytic beta-subunits. *Chem. Biol.* 8, 913-929.

Kidd, D., Liu, Y., and Cravatt, B. F. (2001) Profiling serine hydrolase activities in complex proteomes. *Biochemistry* 40, 4005-4015.

Liu, Y., Patricelli, M. P., and Cravatt, B. F. (1999) Activity-based protein profiling: the serine hydrolases. *Proc. Natl. Acad. Sci. U.S.A* 96, 14694-14699.

Saghatelian, A., Jessani, N., Joseph, A., Humphrey, M., and Cravatt, B. F. (2004) Activity-based probes for the proteomic profiling of metalloproteases. *Proc. Natl. Acad. Sci. U.S.A* 101, 10000-10005.

Schmidinger, H., Hermetter, A., and Birner-Gruenberger, R. (2006) Activity-based proteomics: enzymatic activity profiling in complex proteomes. *Amino Acids* 30, 333-350.

Thornberry, N. A., Peterson, E. P., Zhao, J. J., Howard, A. D., Griffin, P. R., and Chapman, K. T. (1994) Inactivation of interleukin-1β converting enzyme by peptide (acyloxy) methyl ketones. *Biochemistry* 33, 3934-3940.

Wang, C. C., Bozdech, Z., Liu, C. L., Shipway, A., Backes, B. J., Harris, J. L., and Bogyo, M. (2003) Biochemical analysis of the 20 S proteasome of *Trypanosoma brucei*. *J. Biol. Chem.* 278, 15800-15808.

Williams, E. B., Krishnaswamy, S., and Mann, K. G. (1989) Zymogen/enzyme discrimination using peptide chloromethyl ketones. *J. Biol. Chem.* 264, 7536-7545.

Challenge of Differentiating Between Active Versus Inactive Forms of Enzymes

Moldoveanu, T., Hosfield, C. M., Lim, D., Elce, J. S., Jia, Z. C., Davies, P. L. (2002) A Ca(2+) switch aligns the active site of calpain. *Cell* 108, 649-660.

Turk, V., Turk, B., Turk, D. (2001) Lysosomal cysteine proteases: facts and opportunities. *EMBO J.* 20, 4629-4633.

Zymography and Other Reverse Degradomics Technologies

Baragi, V. M. et al. (2000) A versatile assay for gelatinases using succinylated gelatin. *Matrix Biol.* 19, 267-273.

Kaberdin, V. R. and McDowall, K. J. (2003) Expanding the use of zymography by the chemical linkage of small, defined substrates to the gel matrix. *Genome Res.* 13, 1961-1965.

Kleiner, D. E. and Stetler-Stevenson, W. G. (1994) Quantitative zymography: detection of picogram quantities of gelatinases. *Anal. Biochem.* 218, 325-329.

Kupai, K. et al. (2010) Matrix metalloproteinase activity assays: importance of zymography. *J. Pharmacol. Toxicol. Methods* 61, 205-209.

McKerrow, J. H., Pino-Heiss, S., Lindquist, R. and Werb, Z. (1985) Purification and characterization of an elastinolytic proteinase secreted by cercariae of *Schistosoma mansoni*. *J. Biol. Chem.* 260, 3703-3707.

Paemen, L. et al. (1996) The gelatinase inhibitory activity of tetracyclines and chemically modified tetracycline analogues as measured by a novel microtiter assay for inhibitors. *Biochem. Pharmacol.* 52, 105-111.

Piccard, H. et al. (2009) "Reverse degradomics", monitoring of proteolytic trimming by multi-CE and confocal detection of fluorescent substrates and reaction products. *Electrophoresis* 30, 2366-2377.

Vandooren, J. et al. (2011) Gelatin degradation assay reveals MMP-9 inhibitors and function of O-glycosylated domain. *World J. Biol. Chem.* 2, 14-24.

Wilkesman, J. and Kurz, L. (2009) Protease analysis by zymography: a review on techniques and patents. *Recent Pat. Biotechnol.* 3, 175-184.

In Vivo Imaging of Enzyme Activity

Bremer, C., Tung, C. H. & Weissleder, R. In vivo molecular target assessment of matrix metalloproteinase inhibition. *Nat. Med.* 7, 743-748 (2001).

Crawford, B. D. & Pilgrim, D. B. Ontogeny and regulation of matrix metalloproteinase activity in the zebrafish embryo by in vitro and in vivo zymography. *Dev. Biol.* 286, 405-414 (2005).

Kaijzel, E. L., van der Pluijm, G. & Lowik, C. W. Whole-body optical imaging in animal models to assess cancer development and progression. *Clin. Cancer Res.* 13, 3490-3497(2007).

Keow, J. Y., Pond, E. D., Cisar, J. S., Cravatt, B. F. & Crawford, B. D. Activity-based labeling of matrix metalloproteinases in living vertebrate embryos. *PLoS ONE* 7, e43434 (2012).

Saghatelian, A., Jessani, N., Joseph, A., Humphrey, M. & Cravatt, B. F. Activity-based probes for the proteomic profiling of metalloproteases. *Proc. Natl. Acad. Sci. USA* 101, 10000-10005 (2004).

Scherer, R. L., VanSaun, M. N., McIntyre, J. O. & Matrisian, L. M. Optical imaging of matrix metalloproteinase-7 activity in vivo using a proteolytic nanobeacon. *Mol. Imaging* 7, 118-131 (2008).

Weissleder, R., Tung, C. H., Mahmood, U. & Bogdanov, A. Jr. In vivo imaging of tumors with protease-activated near-infrared fluorescent probes. *Nat. Biotechnol.* 17, 375-378 (1999).

Wyatt, R. A. et al. The zebrafish embryo: a powerful model system for investigating matrix remodeling. *Zebrafish* 6, 347-354 (2009).

What is claimed is:

1. A method of identifying protease activity in a complex biological sample, comprising:
   a) incubating the complex sample with a synthetic peptide library and a tag to generate cleavage products;
   b) separating the cleavage products from the complex sample; and
   c) generating a proteolytic signature for the complex sample;
   wherein the synthetic peptide library comprises synthetic charge-changing fluorescent peptide substrates specific for proteases, wherein the charge-changing peptide sequences selectively target proteases selected from coagulation related proteases, metalloproteases, cathepsins, bacterial proteases, kallikreins, and calpains,
   wherein the coagulation related protease is thrombin and the charge-changing peptide sequence has the sequence Ac-N-D-D-Nle-T-P-R-G-S-A-G-A-G-A-G diamino-ethyl-Bodipy FL (BFL),
   wherein the metalloprotease is MMP1 and the charge-changing peptide sequence has the sequence Ac-N-D-G-P-Q-A-I-A-G-Q-G-A-G-diamino-ethyl-BFL,
   wherein the metalloprotease is MMP3 and the charge-changing peptide sequence has the sequence Ac-D-G-P-K-P-V-E-Nva-Y-N-K(ε-BFL)-NH2,
   wherein the metalloprotease is MMP8 and the charge-changing peptide sequence has the sequence set forth in Ac-N-D-G-P-Q-G-Y-A-G-Q-G-A-G diamino-ethyl-BFL,
   wherein the cathepsin is cathepsin-S and the charge-changing peptide sequence has the sequence N-SUC-E-G-R-W-H-T-V-G-L-R-W-E-C(Cy5)-R-CO-NH2,
   wherein the cathepsin is cathepsin-D and the charge-changing peptide sequence has the sequence N-SUC-D-D-L-V-V-L-F-V-K-K-C(Cy5)-A-CO-NH2,
   wherein the bacterial protease is Omp-T and the charge-changing peptide sequence has the sequence Ac-SUC-D-G-D-K-Y-R-R-A-W-G-D-T-I-diamino-ethyl-BFL,
   wherein the bacterial protease is SspB and the charge-changing peptide sequence has the sequence Ac-D-G-D-A-F-S-K-A-L-P-K(ε-BFL)-NH2,
   wherein the kallikrein is kallikrein 2 and the charge-changing peptide sequence has the sequence Ac-N-D-G-D-T-F-R-S-A-A-G-K(ε-BFL)-NH2, wherein the kallikrein is kallikrein 3 and the charge-changing peptide sequence has the sequence Ac-N-D-G-S-I-Y-Q-S-S-T-G-diamino-ethyl-BFL, or wherein the calpain is calpain 1 or calpain 2 and the charge-changing peptide sequence has the sequence N-SUC-E-P-L-F-A-A-R-K($\epsilon$-BFL)-NH2.

2. The method of claim 1, wherein the complex biological sample is selected from blood, plasma, and serum.

3. The method of claim 1, wherein the tag is a fluorescent dye, a radioactive probe, or an affinity tag.

4. The method of claim 1, wherein the cleavage products are separated from the complex sample by gel electrophoresis, capillary electrophoresis, or a combination of DC and AC electrokinetic techniques.

5. The method of claim 1, wherein the substrate signature is generated by detecting and ranking individual substrates in the peptide mixture according to migration.

6. The method of claim 5, wherein the individual substrates are detected via the tag.

7. The method of claim 6, wherein the tag is a fluorescent dye, a radioactive probe, or an affinity tag.

8. The method of claim 1, wherein the proteolytic signature comprises multiple classes of protease activity.

9. The method of claim 8, wherein the multiple classes of protease activity are selected from serine, cysteine, threonine, aspartyl, and metallopeptidase activity.

10. The method of claim 8, wherein the multiple classes of protease activity are detected by separately incubating the complex sample with an activity inhibitor.

11. The method of claim 10, wherein the activity inhibitor is selected from a metal chelator, a cysteine peptidase inhibitor, and an elastase-specific inhibitor.

12. The method of claim 11, wherein the activity inhibitor is selected from EDTA, E-64, CAO74, and a chloromethyl ketone inhibitor.

* * * * *

UNITED STATES PATENT AND TRADEMARK OFFICE
CERTIFICATE OF CORRECTION

PATENT NO. : 11,506,662 B2
APPLICATION NO. : 16/341385
DATED : November 22, 2022
INVENTOR(S) : Michael J. Heller et al.

It is certified that error appears in the above-identified patent and that said Letters Patent is hereby corrected as shown below:

On the Title Page

Column 2, Line 10, Under "OTHER PUBLICATIONS," delete "Afatrix" and insert -- Matrix --.

In the Claims

Column 31, Line 63, in Claim 1, delete "G diamino-" and insert -- G-diamino- --.

Column 32, Line 51, in Claim 1, delete "G diamino-" and insert -- G-diamino- --.

Column 32, Line 64, in Claim 1, delete "-NH)2," and insert -- -NH$_2$, --.

Column 33, Line 3, in Claim 1, delete "S-" and insert -- S-S- --.

Signed and Sealed this
Sixth Day of June, 2023

Katherine Kelly Vidal
*Director of the United States Patent and Trademark Office*

SEQUENCE LISTING

```
<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Norleucine
```

```
<220> FEATURE:
<221> NAME/KEY: MOD_RES
<222> LOCATION: (15)..(15)
<223> OTHER INFORMATION: Gly-diamino-ethyl-BFL

<400> SEQUENCE: 1

Asn Asp Asp Leu Thr Pro Arg Gly Ser Ala Gly Ala Gly Ala Gly
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Gly-diamino-ethyl-BFL

<400> SEQUENCE: 2

Asn Asp Gly Pro Gln Ala Ile Ala Gly Gln Gly Ala Gly
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Norvaline
<220> FEATURE:
<221> NAME/KEY: MOD_RES
<222> LOCATION: (11)..(11)
<223> OTHER INFORMATION: Lys(epsilon-BFL)

<400> SEQUENCE: 3

Asp Gly Pro Lys Pro Val Glu Val Tyr Asn Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Gly-diamino-ethyl-BFL

<400> SEQUENCE: 4

Asn Asp Gly Pro Gln Gly Tyr Ala Gly Gln Gly Ala Gly
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: N-Suc-Glu
<220> FEATURE:
<221> NAME/KEY: MOD_RES
<222> LOCATION: (13)..(13)
<223> OTHER INFORMATION: Cys(Cy5)

<400> SEQUENCE: 5

Glu Gly Arg Trp His Thr Val Gly Leu Arg Trp Glu Cys Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-Suc-Asp
<220> FEATURE:
<221> NAME/KEY: MOD_RES
<222> LOCATION: (11)..(11)
<223> OTHER INFORMATION: Cys(Cy5)

<400> SEQUENCE: 6

Asp Asp Leu Val Val Leu Phe Val Lys Lys Cys Ala
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Suc-Asp
<220> FEATURE:
<221> NAME/KEY: MOD_RES
<222> LOCATION: (13)..(13)
<223> OTHER INFORMATION: Ile-diamino-ethyl-BFL

<400> SEQUENCE: 7

Asp Gly Asp Lys Tyr Arg Arg Ala Trp Gly Asp Thr Ile
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(epsilon-BFL)

<400> SEQUENCE: 8

Asp Gly Asp Ala Phe Ser Lys Ala Leu Pro Lys
1               5                   10

<210> SEQ ID NO 9
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(epsilon-BFL)

<400> SEQUENCE: 9

Asn Asp Gly Asp Thr Phe Arg Ser Ala Ala Gly Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gly-diamino-ethyl-BFL

<400> SEQUENCE: 10

Asn Asp Gly Ser Ser Ile Tyr Gln Ser Ser Thr Gly
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-Suc-Glu
<220> FEATURE:
<221> NAME/KEY: MOD_RES
<222> LOCATION: (8)..(8)
<223> OTHER INFORMATION: Lys(epsilon-BFL)

<400> SEQUENCE: 11

Glu Pro Leu Phe Ala Ala Arg Lys
1               5
```